(12) United States Patent
Short

(10) Patent No.: US 10,562,981 B2
(45) Date of Patent: *Feb. 18, 2020

(54) EXPRESS HUMANIZATION OF ANTIBODIES

(71) Applicant: BioAtla, LLC, San Diego, CA (US)

(72) Inventor: Jay M. Short, Del Mar, CA (US)

(73) Assignee: BioAtla, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/593,721

(22) Filed: May 12, 2017

(65) Prior Publication Data
US 2017/0247473 A1 Aug. 31, 2017

Related U.S. Application Data

(63) Continuation of application No. 13/977,166, filed as application No. PCT/US2011/067589 on Dec. 28, 2011, now Pat. No. 9,683,054.

(60) Provisional application No. 61/428,917, filed on Dec. 31, 2010.

(51) Int. Cl.
C07K 16/46 (2006.01)
C07K 16/24 (2006.01)

(52) U.S. Cl.
CPC .......... *C07K 16/461* (2013.01); *C07K 16/248* (2013.01); *C07K 16/464* (2013.01); *C07K 2317/14* (2013.01); *C07K 2317/24* (2013.01); *C07K 2317/51* (2013.01); *C07K 2317/515* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,381,803 B1 | 3/2008 | Weiner et al. | |
| 8,241,870 B2 * | 8/2012 | Young | C07K 16/00 435/320.1 |
| 9,683,054 B2 * | 6/2017 | Short | C07K 16/461 |
| 2007/0134236 A1 | 6/2007 | De Fougerolles | |
| 2007/0258981 A1 | 11/2007 | Hilbert et al. | |
| 2008/0095772 A1 | 4/2008 | Sato et al. | |
| 2008/0207459 A1* | 8/2008 | Karrer | C07K 16/00 506/1 |
| 2009/0285813 A1 | 11/2009 | Frey et al. | |
| 2010/0008928 A1* | 1/2010 | Sato | C07K 16/3069 424/141.1 |
| 2010/0138945 A1 | 6/2010 | Frey et al. | |

FOREIGN PATENT DOCUMENTS

| | | |
|---|---|---|
| EP | 0239400 | 9/1987 |
| WO | WO03002607 | 1/2003 |
| WO | 2010056948 | 5/2010 |
| WO | 2012092374 | 7/2012 |

OTHER PUBLICATIONS

Krauss et al (Protein Engineering 16: 753-9) (Year: 2003).*
Xiong et al (Biotechnology Advances 26:121-4) (Year: 2008).*
Canadian Office Action; Mailed to CA Agent dated Nov. 1, 2017; Received by U.S. Attorney on Dec. 6, 2017 for CA Application No. CA 2,823,044
Australian Search Report; dated May 25, 2017 for AU Application No. AU2016228196.
International Search Report and Written Opinion for PCT/US2011/0671589, dated Aug. 29, 2012.
Carter, Paul, et al. "Humanization of an anti-p185HER2 antibody for human cancer therapy." Proceedings of the National Academy of Sciences 89.10 (1992): 4285-4289.
Chinese Office Action; dated Sep. 17, 2014 for corresponding CN Application No. 2011800688573.1 with English abstract.
Chinese Office Action; dated May 12, 2015 for corresponding CN Application No. CN201180068857.1 along with English abstract.
Lonberg, N., "Fully Human Antibodies from Transgenic Mouse and Phage Display Platforms;" Current Opinion in Immunology, Elsevier, Oxfor, GB, vol. 20, No. 4, Aug. 1, 2008, pp. 450-459.
Beerli, R. R., et al., "Isolation of Human Monoclonal Antibodies by Mammalian Cell Display," Proceedings of the National Academy of Sciences, National Academy of Sciences, US, vol. 105, No. 38, Sep. 23, 2008, pp. 14336-14341.
Lo Benny, K. C., "Antibody Humanization by CDE Grafting," Methods in Molecular Biolog, Humana Press Inc. NJ, US, vol. 248, Jan. 1, 2004, pp. 135-159.
European Search Report; dated Apr. 2, 2015 for corresponding EP Application No. EP11852441.2.
Restriction Requirement; dated Jun. 7, 2016 for U.S. Appl. No. 13/977,166.
Non-Final Office Action; dated Aug. 24, 2016 for U.S. Appl. No. 13/977,166.
Office Action for Canadian Patent Application No. 2,823,044; dated Jun. 19, 2019.
Boado, Ruben J., et al. "Humanization of anti-human insulin receptor antibody for drug targeting across the human blood-brain barrier." Biotechnology and bioengineering 96.2 (2007): 381-391.
IN Examination Report; Received by Applicant dated Aug. 27, 2018 for In Application No. 6372/DELNP/2013.

(Continued)

*Primary Examiner* — Christopher M Gross
(74) *Attorney, Agent, or Firm* — Mendelsohn Dunleavy, P.C.

(57) ABSTRACT

The disclosure provides a method for generation of humanized full length antibodies in mammalian cells. A library of humanized variants is provided with high, validated human framework diversity without requiring back-mutations to retain original affinity. Synthetic CDR encoding fragment libraries derived from a template antibody are ligated to human framework region encoding fragments from a human framework pool limited only to germline sequences from a functionally expressed antibodies. The vector comprises a nucleic acid sequence encoding HC framework region 4. No CDR grafting or phage display is required.

20 Claims, 5 Drawing Sheets

(56) References Cited

OTHER PUBLICATIONS

Canadian Office Action; Mailed to CA Agent dated Jun. 18, 2018; Received by U.S. Attorney on Jul. 24, 2018 for CA Application No. CA 2,823,044.
Chinese Office Action; dated Jul. 23, 2018 for CN Application No. 201610065918.3.
Notification of the Second Office Action for Chinese Patent Application No. 201610065918.3; dated May 14, 2019.
EP Office Action; dated Dec. 10, 2018 for EP Application No. 16 189 361.5.

* cited by examiner

| Clone | $K_a$ (1/Ms) | $K_d$ (1/s) | $K_D$ (M) |
|---|---|---|---|
| Template | $1.1 \times 10^6$ | $6.2 \times 10^{-5}$ | $57 \times 10^{-12}$ |
| BA001 | $1.31 \times 10^6$ | $3.05 \times 10^{-5}$ | $23 \times 10^{-12}$ |
| h1 = BA399 | $\mathbf{0.973 \times 10^6}$ | $\mathbf{0.53 \times 10^{-5}}$ | $\mathbf{5.4 \times 10^{-12}}$ |
| h2 = BA436 | $1.20 \times 10^6$ | $4.33 \times 10^{-5}$ | $36 \times 10^{-12}$ |
| h3 = BA802 | $1.48 \times 10^6$ | $5.88 \times 10^{-5}$ | $39.6 \times 10^{-12}$ |
| h4 = BA808 | $1.31 \times 10^6$ | $6.59 \times 10^{-5}$ | $50.5 \times 10^{-12}$ |
| h5 = BA840 | $1.01 \times 10^6$ | $23.7 \times 10^{-5}$ | $236 \times 10^{-12}$ |
| h6 = BA848 | $1.25 \times 10^6$ | $15.8 \times 10^{-5}$ | $127 \times 10^{-12}$ |
| h7 = BA890 | $7.45 \times 10^6$ | $6.44 \times 10^{-5}$ | $86.5 \times 10^{-12}$ |
| h8 = BA939 | $1.44 \times 10^6$ | $5.76 \times 10^{-5}$ | $40 \times 10^{-12}$ |

*FIG. 4*

EXPRESS HUMANIZATION OF ANTIBODIES

RELATED APPLICATION DATA

This application is a continuation of U.S. patent application Ser. No. 13/977,166, filed Jun. 28, 2013, which claims priority to International Application No. PCT/US11/67589, filed Dec. 28, 2011, and U.S. Provisional Application No. 61/428,917, filed Dec. 31, 2010, the entire disclosure of which is hereby incorporated by reference as if set forth fully herein.

BACKGROUND OF THE INVENTION

Field of the Invention

The disclosure provides a method for generation of humanized full length antibodies in mammalian cells. A library of humanized variants is provided with high, validated framework diversity without requiring back-mutations to retain original affinity. Synthetic CDR encoding fragment libraries derived from a template antibody are ligated to human framework region encoding fragments from a human framework pool limited only to germline sequences from a functionally expressed antibodies. The vector comprises a nucleic acid sequence encoding HC framework region 4. No CDR grafting or phage display is required.

Description of the Related Art

Monoclonal antibodies (MAbs) are monospecific for a particular antigen and are made by identical immune cells that are clones of a unique parent cell. Monoclonal antibodies traditionally are made by fusing myeloma cells with spleen cells from a mouse that has been immunized with the desired antigen. Fused hybrid cells, or hybridomas, can be grown indefinitely in cell culture media, or can be injected in mice where they produce tumors containing an antibody rich fluid called ascites fluid. Antibodies can then be purified from the cell culture medium or ascites.

Monoclonal antibody therapy is the use of MAbs to specifically bind to an antigen, for example, a cell surface antigen on a target cell. This may stimulate the patient's immune system to attack those cells. MAbs have been developed to treat various diseases such as rheumatoid arthritis, multiple sclerosis and different types of cancers. Initially, murine antibodies were obtained with hybridoma technology; however the dissimilarity between murine and human immune systems resulted in several clinical failure of these antibodies. Nevertheless, a small number of murine MAbs are FDA approved to treat various conditions. Muromonab-CD3 (Orthoclone OKT3) is a murine MAb that targets the T cell CD3 receptor and was approved in 1986 for transplant rejection. Tositumoman (Bexxar) is a murine Mab that targets CD20 and was approved in 2003 for the treatment of Non-Hodgkin lymphoma.

Therapeutic deficiencies of mouse monoclonal antibodies as human therapeutics are well known and include short in vivo half life, weak effector functions mediated by the mouse heavy chain constant region; patient sensitization to the antibody, and generation of a human anti-mouse antibody (HAMA) response; and neutralization of the mouse antibody by HAMA leading to a loss of therapeutic efficiency. See, for example, Williams et al. 2010, Humanising antibodies by CDR grafting. Antibody Engineering, Edit by R. Kontermann and S. Dubel, Springer Lab Manual, 319-339. One major obstacle in early development of therapeutic antibodies was the human anti-murine antibody (HAMA) response which occurred in up to about 50% of patients upon administration of murine hybridoma-derived antibodies and compromised the safety, efficacy and half-life of the antibody therapeutics.

One way to alleviate certain deficiencies of mouse monoclonal antibodies is antibody humanization. Various techniques of antibody humanization are known. One method of antibody humanization is chimerization. In mouse/human chimeric antibodies, the immunogenic murine constant domains are replaced by the human counterpart. Intact murine variable domains are preserved to maintain the intrinsic antigen-binding affinity; i.e., the entire Fv regions were retained from the murine antibody (about 66% human) Antibody chimerization was found to alleviate the short in vivo half-life compared to the murine MAb, and impart human Fc effector function on the antibody. Although chimerization of some murine antibodies resulted in reduced HAMA response, others remained immunogenic. A few chimeric antibodies are FDA approved to treat various conditions. Abciximab (ReoPro), is a chimeric antibody which targets inhibition of glycoprotein IIb/IIIa and was FDA approved in 1994 for the treatment of cardiovascular disease. Infliximab (Remicade) is a chimeric antibody that results in inhibition of TNF-alpha signaling; was first approved in 1998 and is now used for the treatment of several autoimmune disorders.

A second technique of antibody humanization termed CDR grafting involves the transplantation of the entire murine CDRs onto a human framework region wherein the reshaped humanized antibody only retained essential binding elements from the murine antibody (5-10% of the total sequence). For example, see Lo, Antibody humanization by CDR grafting. Antibody Engineering, Methods and protocols. Edit by Benny K. C. Lo, Methods in Molecular Biology, 2004, 248, 135-159. CDR grafting is described in U.S. Pat. Nos. 5,225,539 and 5,585,089, each of which is incorporated herein by reference. Humanized antibodies from CDR grafting resulted in increased in vivo tolerance and efficacy of therapeutic antibodies. According to Lo 2004, the key to successful CDR grafting lies in the preservation of the murine CDR conformations in the reshaped antibody for antigen binding. The antibody Fv region comprises variable domains from the light chain ($V_L$) and the heavy chain ($V_H$) and confers antibodies with antigen-binding specificity and affinity. The variable domains adopt the immunoglobulin fold in which two antiparallel beta-sheet framework scaffolds support three hypervariable CDRs. Unfortunately, CDR grafting often leads to suboptimal orientations of the murine CDR loops responsible for antigen binding. Therefore, critical murine framework residues needed to be reintroduced as back-mutations to restore the optimum CDR conformations for antigen binding. According to Williams et al. 2010, ibid., at least 118 antibodies have been humanized. Of the 24 approved antibodies on the market, 13 are humanized, four are murine, five are chimeric and two are human. The marketed, humanized antibodies were all generated by CDR grafting.

Another technique for developing a minimally immunogenic humanized antibody is known as SDR grafting. Some humanized antibodies were found to elicit an anti-idiotype (anti-Id) response against the potentially immunogenic murine CDRs. Further, it was found that not all of the CDRs are equally important, or even essential, for antigen binding. It was also found that only about 20-33% of CDR residues are involved in antigen contact. The CDR residues that are most important in antigen-antibody interaction are called specificity-determining residues (SDRs). SDRs are found at positions of high variability and may be determined by determination of the three-dimensional structure of the antigen-antibody complex or by genetic manipulation of the antibody-combining site. See for example, Kashmiri et al., 2004, Developing a minimally immunogenic humanized antibody by SDR grafting. Antibody Engineering, Methods and protocols. Edit by Benny K. C. Lo, Methods in Molecular Biology, 248, 361-376. Therefore, there is room for protein evolution within the CDR regions while maintaining affinity for the target antigen.

Competing technologies exist to reduce the immunogenicity of antibodies. Transgenic mice (e.g. Xenomouse and UltiMAb-Mouse) containing large parts of the the human immunoglobulin locus, can be a source of "fully human" antibodies. Human antibodies derived from a bacteriophage library of human variable regions also need no humanization, but frequently need further mutation to achieve high binding potency. A relatively small number of marketed antibodies have been derived using these other platform technologies. See Williams et al. 2010, ibid.

According to Lo 2004, the goal of antibody humanization is to engineer a monoclonal antibody (MAb) raised in a non-human species into one that is less immunogenic when administered to humans. However, it would be advantageous to develop a technique of antibody humanization that is accompanied by various protein evolutionary techniques to produce a humanized antibody with other optimized characteristics such as enhanced affinity for the target antigen compared to the mouse and/or increased expression.

SUMMARY OF THE INVENTION

The disclosure provides methods of express, rapid humanization of antibodies. One or more libraries of full length antibodies are generated and simultaneously screened for binding and expression optimization. The antibody libraries are specifically designed to be small in member number, but highly diverse. Only validated human frameworks are employed in the antibody libraries, which have been functionally expressed from germline sequences. A subset of germline sequences are specifically selected for maximum diversity in the final library. In one aspect, a single sequence for LC and HC Framework 4 is employed for the entire library, and DNA encoding this framework sequence is built into the vector. Ligation is used to recombine frameworks and CDRs, thus avoiding overlap PCR which requires multiple primer sets. In one aspect, the library is expressed and screened in the manufacturing host. In another aspect, an antibody equal to or superior to the donor antibody, for example a mouse MAb, in terms of antigen affinity is identified in three to four months.

In one embodiment, the disclosure provides a method of producing a humanized antibody comprising the step of synthesizing immunoglobulin heavy chain (HC) double stranded DNA fragment libraries comprising complementarity determining region (CDR) fragment encoding libraries and framework (FW) fragment encoding libraries, wherein at least one CDR fragment library is derived from the template antibody and each FW fragment library is from a human framework pool obtained from functionally expressed human antibodies.

In one aspect, the disclosure provides a method of producing a humanized antibody comprising the step of synthesizing immunoglobulin light chain (LC) double stranded DNA fragment libraries comprising CDR fragment encoding libraries and FW fragment encoding libraries, wherein at least one CDR fragment library is derived from the template antibody and each FW fragment library is from a human framework pool obtained from functionally expressed human antibodies.

In another aspect, the disclosure provides a method of producing a humanized antibody comprising the step of producing a humanized antibody further comprises assembling from the HC fragment libraries by stepwise liquid phase ligation of heavy chain FW encoding fragments and CDR encoding fragments in the order of: FW1-CDR1-FW2-CDR2-FW3-CDR3 to produce a humanized HC variable domain encoding library.

In a further aspect, the disclosure provides a method of producing a humanized antibody comprising the step of producing a humanized antibody further comprises assembling from the LC fragment libraries by stepwise liquid phase ligation of light chain FW encoding fragments and CDR encoding fragments in the order of: FW1-CDR1-FW2-CDR2-FW3-CDR3 to produce a humanized LC variable domain encoding library.

In another aspect, the disclosure provides a method of producing a humanized antibody comprising the steps of cloning the assembled humanized heavy chain variable domain library and the assembled light chain variable domain library into an expression vector to create a humanization library; transfecting the humanization library into cells; and expressing full length humanized antibodies in the cells to create a humanized antibody library.

In further aspects, the disclosure provides a method of producing a humanized antibody comprising the steps of screening the humanized antibody library to determine the expression level of the humanized antibodies; and screening the humanized antibody library to determine the affinity of the humanized antibodies for the antigen compared to the affinity of the template antibody to the antigen. In one aspect, the humanized antibody exhibits equal or greater affinity for an antigen compared to a template antibody.

In one aspect, the disclosure provides a method of producing a humanized antibody comprising the step of cloning the assembled humanized heavy chain variable domain library and the assembled light chain variable domain library into an expression vector comprising a nucleic acid sequence encoding HC framework region 4. In a specific aspect, the nucleotide sequence encoding framework 4 is derived from a human heavy chain variable domain derived from a functionally expressed human antibody.

In another aspect, the vector comprises a nucleic acid sequence encoding LC framework region 4. In a specific aspect, the nucleotide sequence encoding framework 4 is derived from a human light chain variable domain derived from a functionally expressed human antibody.

In various aspects, the disclosure provides a method of producing a humanized antibody library wherein the member number of the humanized antibody library is 10,000,000 members or fewer; 1,000,000 members or fewer; or 100,000 members or fewer.

In one aspect, the disclosure provides a method of producing a humanized antibody comprising the step of cloning the assembled humanized HC variable domain library into an expression vector to create a vector-HC variable domain DNA library, and ligating the assembled light chain variable domain library into the vector-HC library to create the humanization library. In another aspect, the expression step comprises expressing both the humanized heavy chain variable domain and the humanized light chain variable domain from a single promoter.

In another aspect, the disclosure provides a method of producing a humanized antibody comprising a step of screening the humanized antibody library for a humanized antibody having one or more additional improved characteristics when compared to the template antibody; the one or more characteristics selected from the group consisting of: equilibrium dissociation constant ($K_D$); stability; melting temperature ($T_m$); pI; solubility; expression level; reduced immunogenicity and improved effector function. In certain aspects, the improvement is between about 1% and 500%, relative to the template antibody or is between about 2 fold and 1000 fold relative to the template antibody.

In another aspect, the disclosure provides a method of producing a humanized antibody further comprising the step of cloning the assembled humanized heavy chain variable domain library and the assembled light chain variable domain library into an expression vector to create a humanization library; and transfecting the humanization library into cells; wherein the cells are selected from a eukaryotic cell production host cell line selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells; S. cerevisiae yeast cells; and picchia yeast cells. In specific aspects, the eukaryotic cell production host cell line is selected from CHO-S; HEK293; CHOK1SV or NS0. In another aspect, the cell is a eukaryotic cell production host with antibody cell surface display and, optionally, one or more of the screening steps are performed in the eukaryotic cell production host.

In one embodiment, the disclosure provides a method of producing a humanized antibody comprising screening a humanized library utilizing an assay selected from quantitative ELISA; affinity ELISA; ELISPOT; flow cytometry, immunocytology, Biacore® surface plasmon resonance analysis, Sapidyne KinExA™ kinetic exclusion assay; SDS-PAGE; Western blot, or HPLC.

BRIEF DESCRIPTION OF THE DRAWINGS

FIG. 4 shows binding affinity BiaCore surface plasmon resonance data for humanized anti-IL6 antibodies compared to a template antibody. Data for the template, CNTO328, a chimeric, human-murine antibody, is from US 2006/0257407, which is incorporated herein by reference. BA001 is also a template antibody that has the same sequence as the template CNTO328, but was manufactured in a different expression system. Humanized variant antibodies h1-h8 were obtained with no additional affinity maturation.

DEFINITION OF TERMS

Figure 1:
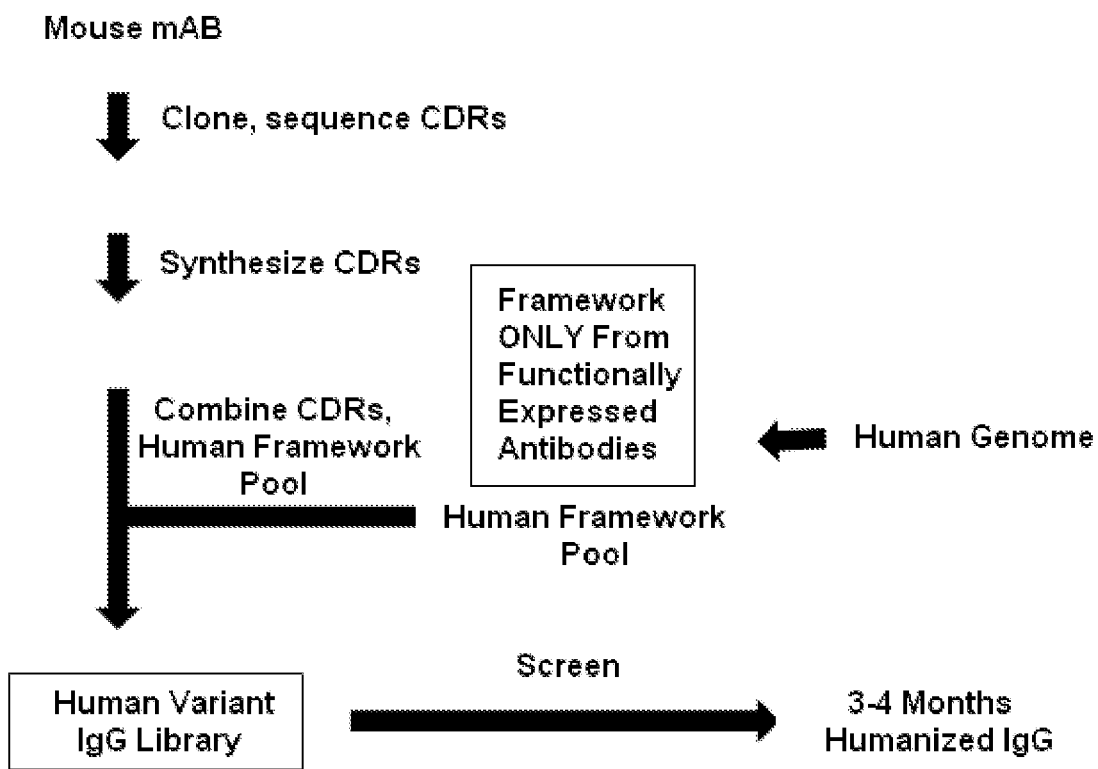
FIG. 1 shows a schematic of the method of rapid antibody humanization of a template antibody.

In order to facilitate understanding of the examples provided herein, certain frequently occurring methods and/or terms will be described.

The term "affinity maturation" refers to the increase in average affinity of an immune response for an antigen. In nature, it can occur after repeated exposure to an antigen. A particularly preferred type of substitutional variant involves substituting one or more hypervariable region residues of a parent antibody (e.g. human antibody). Generally, the resulting variant(s) selected for further development will have improved biological properties relative to the parent antibody from which they are generated. A convenient way for generating such substitutional variants involves affinity maturation using techniques described herein or other techniques known to one of skill in the art, for example, phage display (Schier R., J. Mol. Biol., 263:551-67, 1996). The variants are then screened for their biological activity (e.g. binding affinity) as described herein, e.g. Biacore analysis. In order to identify hypervariable region residues which would be good candidates for modification, alanine scanning mutagenesis can be performed to identify hypervariable region residues contributing significantly to antigen binding. Antibodies with superior properties in one or more relevant assays can undergo further development.

The term "agent" is used herein to denote an antibody or antibody library. Agents are evaluated for potential activity as, for example, anti-neoplastics, anti-inflammatories or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "amino acid" as used herein refers to any organic compound that contains an amino group ($-NH_2$) and a carboxyl group ($-COOH$); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gln or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" means that the number of copies of a polynucleotide is increased.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

A single chain antibody ("SCA") is a genetically engineered single chain molecule containing the variable region of a light chain and the variable region of a heavy chain, linked by a suitable, flexible polypeptide liner.

The term "biosimilar", also termed "follow-on biologic", refers to officially approved new versions of innovator biopharmaceutical products, following patent or exclusivity expiry.

The term "cell production host", or "manufacturing host", refers to a cell line used for the production or manufacturing of proteins. Eukaryotic cells such as mammalian cells, including, but not limited to human, mouse, hamster, rat, monkey cell lines as well as yeast, insect and plant cell lines. Prokaryotic cells can alternatively be utilized. In one aspect, a mammalian cell production host is selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells. In another aspect, the cell production host is a GS-NS0 or GS-CHOK1 cell line. In another aspect, the cell production host is selected from *S. cerevisiae* yeast cells; and picchia yeast cells. In another aspect, the cell production host is a bacterial cell line.

A molecule that has a "chimeric property" is a molecule that is: 1) in part homologous and in part heterologous to a first reference molecule; while 2) at the same time being in part homologous and in part heterologous to a second reference molecule; without 3) precluding the possibility of being at the same time in part homologous and in part heterologous to still one or more additional reference molecules. In a non-limiting embodiment, a chimeric molecule may be prepared by assembling a reassortment of partial molecular sequences. In a non-limiting aspect, a chimeric polynucleotide molecule may be prepared by synthesizing the chimeric polynucleotide using plurality of molecular templates, such that the resultant chimeric polynucleotide has properties of a plurality of templates.

The term "cognate" as used herein refers to a gene sequence that is evolutionarily and functionally related between species. For example, but not limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

The term "commercial scale" means production of a protein or antibody at a scale appropriate for resale.

A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482 by the homology alignment algorithm of Needlemen and Wuncsch J. Mol. Biol. 48: 443 (1970), by the search of similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

As used herein, the term "complementarity-determining region" and "CDR" refer to the art-recognized term as exemplified by the Kabat and Chothia. CDR definitions are also generally known as supervariable regions or hypervariable loops (Chothia and Leks, 1987; Clothia et al., 1989; Kabat et al., 1987; and Tramontano et al., 1990). Variable region domains typically comprise the amino-terminal approximately 105-115 amino acids of a naturally-occurring immunoglobulin chain (e.g., amino acids 1-110), although variable domains somewhat shorter or longer are also suitable for forming single-chain antibodies. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. H means the variable heavy chain and L means the variable light chain. The CDR regions of an Ig-derived region may be determined as described in Kabat (1991). Sequences of Proteins of Immunological Interest, 5th edit., NIH Publication no. 91-3242 U.S. Department of Health and Human Services, Chothia (1987) J. Mol. Biol. 196, 901-917 and Chothia (1989) Nature, 342, 877-883.

The term "comprehensive" is used herein to refer to a technique of evolution wherein every possible change is made at each position of a template polynucleotide or template polypeptide and the polynucleotide or polypeptide is tested to confirm the intended change has been made by sequencing or some other technique. Comprehensive mutagenesis refers to mutating the DNA of a region of a gene encoding a protein that changes codon amino acid sequence of the protein and then determining via sequencing or other technologies that all mutations have been made and in the optimal case arrayed where every clone is in an identifiable position and/or uniquely tagged. Then screening of all of the expressed mutants is performed to ensure that all are expressed comprehensively for an improved phenotype in order to provide guaranteed comprehensive coverage, i.e. CPE library with Comprehensive Screening comprising the BioAtla CPE process. Non-expressing clones in the screening system will also be simultaneously measured for expression to ensure that are not incorrectly labeled as negative or neutral mutations once enabled for expression an alternative system such as in vitro transcription and translation. Alternatively, sequencing could be performed on all clones after screening, but it should include all negative, neutral and up-mutant clones. Any mutants not identified are then be added in a second round of screening to yield and a true comprehensive mutagenesis and screening expression/activity system such as CPE. This is enabled in part by recent successes in high throughput sequencing that did not exist previously.

The term "Comprehensive Positional Evolution" (CPE™) is used to describe an antibody evolution technology platform that can be used to combine comprehensive mutagenesis, shuffling and synthesis technologies to enhance single or multiple antibody properties and binding characteristics. The CPE platform allows for the comprehensive mapping of the in vivo effects of every individual codon change within the protein for all 63 potential codon changes at each position within the protein. This comprehensive mutagenesis technology rapidly generates antibody variants by testing amino acid changes at every position along an antibody variable domain's sequence.

The term "Combinatorial Protein Synthesis" (CPS™) is used to describe combinatorial protein synthesis technologies that can be used to optimize the desired characteristics of antibodies by combining their best properties into a new, high-performance antibody. CPS™ can be used following CPE™ and can allow for the subsequent generation and in vivo selection of all permutations of improved individual codons for identification of the optimal combination or set of codon changes within a protein or antibody. The combination of these technologies can significantly expand the pool of antibody variants available to be screened and it significantly increases the probability of finding antibodies with single or multiple enhanced characteristics such as binding affinity, specificity, thermo-stability, expression level, effector function, glycosylation, and solubility.

For full length antibody molecules, the immunoglobulin genes can be obtained from genomic DNA or mRNA of hybridoma cell lines. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "degrading effective" amount refers to the amount of which is required to process at least 50% of the substrate, as compared to substrate not contacted with the enzyme. Preferably, at least 80% of the substrate is degraded.

As used herein, the term "defined sequence framework" refers to a set of defined sequences that are selected on a non-random basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)10$ sequences, and (2) a pseudorandom 10-mer sequence of the 20 conventional amino acids can be any of $(20)10$ sequences but will exhibit a bias for certain residues at certain positions and/or overall, (3) a defined sequence kernal is a subset of sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. Of illustration and not limitation, the sequences (NNK)10 and (NNM)10, wherein N represents A, T, G, or C; K represents G or T; and M represents A or C, are defined sequence kernels.

The term "deimmunization" as used herein relates to production of a variant of the template binding molecule, which is modified compared to an original wild type molecule by rendering said variant non-immunogenic or less immunogenic in humans. Deimmunized molecules according to the invention relate to antibodies or parts thereof (like frameworks and/or CDRs) of non-human origin. Corresponding examples are antibodies or fragments thereof as described in U.S. Pat. No. 4,361,549. The term "deimmunized" also relates to molecules, which show reduced propensity to generate T cell epitopes. In accordance with this invention, the term "reduced propensity to generate T cell epitopes" relates to the removal of T-cell epitopes leading to specific T-cell activation.

Furthermore, reduced propensity to generate T cell epitopes means substitution of amino acids contributing to the formation of T cell epitopes, i.e. substitution of amino acids, which are essential for formation of a T cell epitope. In other words, reduced propensity to generate T cell epitopes relates to reduced immunogenicity or reduced capacity to induce antigen independent T cell proliferation. In addition, reduced propensity to generate T cell epitopes relates to deimmunization, which means loss or reduction of potential T cell epitopes of amino acid sequences inducing antigen independent T cell proliferation.

The term "T cell epitope" as used herein relates to short peptide sequences which can be released during the degradation of peptides, polypeptide or proteins within cells and subsequently be presented by molecules of the major histocompatibility complex (MHC) in order to trigger the activation of T cells; see inter alia WO 02/066514. For peptides presented by MHC class II such activation of T cells can then induce an antibody response by direct stimulation of B cells to produce said antibodies.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. Shuffling may be random or non-random.

As used in this invention, the term "epitope" refers to an antigenic determinant on an antigen, such as a phytase polypeptide, to which the paratope of an antibody, such as a phytase-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

The term "evolution" refers to a change in at least one property, characteristic or activity of a genetically or synthetically modified antibody when compared to a template antibody.

The terms "fragment", "derivative" and "analog" when referring to a reference polypeptide comprise a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

The term "fragment" when applied to a nucleic acid sequence refers to a molecule that encodes for a portion, or a sub-portion, of an antibody molecule. For example, an HC CDR1 DNA fragment, may encode the entire heavy chain CDR1, or a truncated portion thereof.

In one aspect, certain methods provided herein provide for producing from a template polypeptide a set of progeny polypeptides in which a "full range of single amino acid substitutions" is represented at each amino acid position. As used herein, "full range of single amino acid substitutions" is in reference to the naturally encoded 20 naturally encoded polypeptide-forming alpha-amino acids, as described herein.

The term "gene" means the segment of DNA involved in producing a polypeptide chain; it includes regions preceding and following the coding region (leader and trailer) as well as intervening sequences (introns) between individual coding segments (exons).

"Genetic instability", as used herein, refers to the natural tendency of highly repetitive sequences to be lost through a process of reductive events generally involving sequence simplification through the loss of repeated sequences. Deletions tend to involve the loss of one copy of a repeat and everything between the repeats.

The term "heterologous" means that one single-stranded nucleic acid sequence is unable to hybridize to another single-stranded nucleic acid sequence or its complement. Thus, areas of heterology means that areas of polynucleotides or polynucleotides have areas or regions within their sequence which are unable to hybridize to another nucleic acid or polynucleotide. Such regions or areas are for example areas of mutations.

The term "homologous" or "homeologous" means that one single-stranded nucleic acid nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The term "humanized" is used to describe antibodies wherein complementarity determining regions (CDRs) from a mammalian animal, e.g., a mouse, are combined with a human framework region. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. In another aspect, besides mouse antibodies, other species can be humanized, such as, for example, other rodent, camel, rabbit, cat, dog, pig, horse, cow, fish, llama and shark. In a broad aspect, any species that produces antibodies can be utilized in the production of humanized antibodies. Additionally, the antibodies of the invention may be chimeric, human-like, humanized or fully human, in order to reduce their potential antigenicity, without reducing their affinity for their target. Chimeric, human-like and humanized antibodies have generally been described in the art. By incorporating as little foreign sequence as possible in the hybrid antibody, the antigenicity is reduced. Preparation of these hybrid antibodies may be carried out by methods well known in the art.

An immunoglobulin light or heavy chain variable region consists of a "framework" region interrupted by three hyper-variable regions, also called CDR's. The extent of the framework region and CDR's have been precisely defined (see, "Sequences of Proteins of Immunological Interest," Kabat et al., 1987). The sequences of the framework regions of different light or heavy chains are relatively conserved within a species. As used herein, a "human framework region" is a framework region that is substantially identical (about 85 or more, usually 90-95 or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

In accordance with this invention, a framework region relates to a region in the V domain (VH or VL domain) of immunoglobulins that provides a protein scaffold for the hypervariable complementarity determining regions (CDRs) that make contact with the antigen. In each V domain, there are four framework regions designated FR1, FR2, FR3 and FR4. Framework 1 encompasses the region from the N-terminus of the V domain until the beginning of CDR1, framework 2 relates to the region between CDR1 and CDR2, framework 3 encompasses the region between CDR2 and CDR3 and framework 4 means the region from the end of CDR3 until the C-terminus of the V domain; see, inter alia, Janeway, Immunobiology, Garland Publishing, 2001, 5th ed. Thus, the framework regions encompass all the regions outside the CDR regions in VH or VL domains. In one aspect of the disclosure, a single sequence is employed for framework 4 which is held constant through each member of the antibody library. In one aspect, the single sequence encoding framework region 4 is the most common sequence found in a human framework pool limited only to germline sequences from a functionally expressed antibodies.

The person skilled in the art is readily in a position to deduce from a given sequence the framework regions and, the CDRs; see Kabat (1991) Sequences of Proteins of Immunological Interest, 5th edit., NIH Publication no. 91-3242 U.S. Department of Health and Human Services, Chothia (1987) J. Mol. Biol. 196, 901-917 and Chothia (1989) Nature, 342, 877-883.

The benefits of this invention extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide or the polynucleotide.

The term "isolated" means that the material is removed from its original environment (e.g., the natural environment if it is naturally occurring). For example, a naturally-occurring polynucleotide or protein present in a living animal is not isolated, but the same polynucleotide or protein, separated from some or all of the coexisting materials in the natural system, is isolated. Such polynucleotides could be part of a vector and/or such polynucleotides or proteins could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

"Ligation" refers to the process of forming phosphodiester bonds between two double stranded nucleic acid fragments (Maniatis et al., 1982, p. 146). Unless otherwise provided, ligation may be accomplished using known buffers and conditions with 10 units of T4 DNA ligase ("ligase") per 0.5 µg of approximately equimolar amounts of the DNA fragments to be ligated.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

The term "mammalian cell surface display" refers to a technique whereby a protein or antibody, or a portion of an antibody, is expressed and displayed on a mammalian host cell surface for screening purposes; for example, by screening for specific antigen binding by a combination of magnetic beads and fluorescence-activated cell sorting. In one aspect, mammalian expression vectors are used for simultaneous expression of immunoglobulins as both a secreted and cell surface bound form as in DuBridge et al., US 2009/0136950, which is incorporated herein by reference. In another aspect, the techniques of Gao et al. are employed for a viral vector encoding for a library of antibodies or antibody fragments are displayed on the cell membranes when expressed in a cell as in Gao et al., US 2007/0111260, incorporated herein by reference. Whole IgG surface display on mammalian cells is known. For example, a Akamatsu et al. developed a mammalian cell surface display vector, suitable for directly isolating IgG molecules based on their antigen-binding affinity and biological activity. Using an Epstein-Barr virus-derived episomal vector, antibody libraries were displayed as whole IgG molecules on the cell surface and screened for specific antigen binding by a combination of magnetic beads and fluorescence-activated cell sorting. Plasmids encoding antibodies with desired binding characteristics were recovered from sorted cells and converted to the form for production of soluble IgG. Akamatsuu et al. J. Immunol. Methods 2007 327(1-2):40-52; incorporated herein by reference. Ho et al. used human embryonic kidney 293T cells that are widely used for transient protein expression for cell surface display of single-chain Fv antibodies for affinity maturation. Cells expressing a rare mutant antibody with higher affinity were enriched 240-fold by a single-pass cell sorting from a large excess of cells expressing WT antibody with a slightly lower affinity. Furthermore, a highly enriched mutant was obtained with increased binding affinity for CD22 after a single selection of a combinatory library randomizing an intrinsic antibody hotspot. Ho et al. Isolation of anti-CD22 Fv with high affinity by Fv display on human cells, Proc Natl Acad Sci USA 2006 Jun. 20; 103(25): 9637-9642; incorporated herein by reference.

Beerli et al. used B cells specific for an antigen of interest which were directly isolated from peripheral blood mononuclear cells (PBMC) of human donors. Recombinant, antigen-specific single-chain Fv (scFv) libraries are generated from this pool of B cells and screened by mammalian cell surface display by using a Sindbis virus expression system. This method allows isolating antigen-specific antibodies by a single round of FACS. The variable regions (VRs) of the heavy chains (HCs) and light chains (LCs) were isolated from positive clones and recombinant fully human antibodies produced as whole IgG or Fab fragments. In this manner, several hypermutated high-affinity antibodies binding the Qβ virus like particle (VLP), a model viral antigen, as well as antibodies specific for nicotine were isolated. All antibodies showed high expression levels in cell culture. The human nicotine-specific mAbs were validated preclinically in a mouse model. Beerli et al., Isolation of human monoclonal antibodies by mammalian cell display, Proc Natl Acad Sci USA. 2008 Sep. 23; 105(38): 14336-14341; incorporated herein by reference.

Yeast cell surface display is also known, for example, see Kondo and Ueda 2004, Yeast cell-surface display-applications of molecular display, Appl. Microbiol. Biotechnol., 64(1): 28-40, which describes for example, a cell-surface engineering system using the yeast *Saccharomyces cerevisiae*. Several representative display systems for the expression in yeast *S. cerevisiae* are described in Lee et al, 2003, Microbial cell-surface display, TRENDS in Bitechnol. 21(1): 45-52. Also Boder and Wittrup 1997, Yeast surface display for screening combinatorial polypeptide libraries, Nature Biotechnol., 15(6): 553.

The term "manufacturing" refers to production of a protein at a sufficient quantity to permit at least Phase I clinical testing of a therapeutic protein, or sufficient quantity for regulatory approval of a diagnostic protein.

The term "missense mutation" refers to a point mutation where a single nucleotide is changed, resulting in a codon that codes for a different amino acid. Mutations that change an amino acid to a stop codon are called nonsense mutations.

As used herein, a "molecular property to be evolved" includes reference to molecules comprised of a polynucleotide sequence, molecules comprised of a polypeptide sequence, and molecules comprised in part of a polynucleotide sequence and in part of a polypeptide sequence. Particularly relevant—but by no means limiting—examples of molecular properties to be evolved include enzymatic activities at specified conditions, such as related to temperature; salinity; pressure; pH; and concentration of glycerol, DMSO, detergent, and/or any other molecular species with which contact is made in a reaction environment. Additional particularly relevant—but by no means limiting examples of molecular properties to be evolved include stabilities—e.g., the amount of a residual molecular property that is present after a specified exposure time to a specified environment, such as may be encountered during storage.

The term "Multidimensional Epitope Mapping" (MEM) refers to the identification of the epitope and the resolution of the amino acids that are important for antibody binding. Information about the binding sites (epitopes) of proteins recognized by antibodies is important for their use as biological or diagnostic tools as well as for understanding their mechanisms of action. However, antigens are highly diverse, in their primary sequence as well as in three dimensional structures. Epitopes generally fall into 3 categories: 1) linear epitopes, i.e. the antibody binds to residues on a linear part of the polypeptide chain, 2) conformational epitopes, where the binding site is formed by a structural element (e.g. α-helix, loop), 3) discontinuous epitopes where two or more separate stretches of the polypeptide chain which are brought together in the three dimensional structure of the antigen form the binding surface.

The term "mutating" refers to creating a mutation in a nucleic acid sequence; in the event where the mutation occurs within the coding region of a protein, it will lead to a codon change which may or may not lead to an amino acid change.

The term "mutations" means changes in the sequence of a wild-type nucleic acid sequence or changes in the sequence of a peptide or polypeptides. Such mutations may be point mutations such as transitions or transversions. The mutations may be deletions, insertions or duplications.

As used herein, the degenerate "N,N,G/T" nucleotide sequence represents 32 possible triplets, where "N" can be A, C, G or T.

As used herein, the degenerate "N,N,N" nucleotide sequence represents 64 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (un-diseased) individual, such as would be typical for the species.

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular protein—as well as other synonymous terms—refer to a DNA sequence which is transcribed and translated into a protein when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an protein" or "DNA encoding an protein" or "polynucleotide encoding an protein" and other synonymous terms encompasses a polynucleotide which includes only coding sequence for the protein as well as a polynucleotide which includes additional coding and/or non-Cq3 coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable to its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting—aspect, a nucleotide construct is exemplified by a DNA expression DNA expression constructs suitable for the transformation of a host cell.

An "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45° C. and 0.001-10 mM divalent cation (e.g., Mg++, Ca++); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants.

The term "population" as used herein means a collection of components such as polynucleotides, portions or polynucleotides or proteins. A "mixed population: means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g., glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modification (e.g. two proteolytic cleavages, or a proteolytic cleavage and a deglycosylation) can be distinguished en route to the production of a mature molecule, the reference precursor molecule may be termed a "pre-pro-form" molecule.

A "property" can describe any characteristic, including a physical, chemical, or activity characteristic property of a protein or antibody to be optimized. For example, in certain aspects, the predetermined property, characteristic or activity to be optimized can be selected from is selected from reduction of protein-protein aggregation, enhancement of protein stability, increased protein solubility, increased protein pH stability, increased protein temperature stability, increased protein solvent stability, increased selectivity, decreased selectivity, introduction of glycosylation sites, introduction of conjugation sites, reduction of immunogenicity, enhancement of protein expression, increase in antigen affinity, decrease in antigen affinity, change in binding affinity, change in immunogenicity, change in catalytic activity, pH optimization, or enhancement of specificity. Other properties or characteristics to be optimized include antibody stability in vivo (e.g., serum half-lives) and/or in vitro (e.g., shelf-life); melting temperature (Tm) of the antibody (e.g., as determined by differential scanning calorimetry (DSC) or other method known in the art), the pI of the antibody (e.g., as determined Isoelectric focusing (IEF) or other methods known in the art); solubility; binding properties (e.g., antibody-antigen binding constants such as, Ka, Kd, $K_{on}$, $K_{off}$), equilibrium dissociation constant ($K_D$); antibody solubility (e.g., solubility in a pharmaceutically acceptable carrier, diluent or excipient), effector function (e.g., antibody dependent cell-mediated cytotoxicity (ADCC)); expression level and production levels (e.g., the yield of an antibody from a cell).

An "optimized" property refers to a desirable change in a particular property in a mutant protein or antibody compared to a template antibody. In one aspect, an optimized property refers to wherein the improvement is between about 1% and 500%, relative to the template antibody or is between about 2 fold and 1000 fold, relative to the template antibody.

As used herein, the term "pseudorandom" refers to a set of sequences that have limited variability, such that, for example, the degree of residue variability at another position, but any pseudorandom position is allowed some degree of residue variation, however circumscribed.

"Quasi-repeated units", as used herein, refers to the repeats to be re-assorted and are by definition not identical. Indeed the method is proposed not only for practically identical encoding units produced by mutagenesis of the identical starting sequence, but also the reassortment of similar or related sequences which may diverge significantly in some regions. Nevertheless, if the sequences contain sufficient homologies to be reasserted by this approach, they can be referred to as "quasi-repeated" units.

As used herein "random peptide library" refers to a set of polynucleotide sequences that encodes a set of random peptides, and to the set of random peptides encoded by those polynucleotide sequences, as well as the fusion proteins contain those random peptides.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

"Recombinant" proteins refer to enzymes produced by recombinant DNA techniques, i.e., produced from cells transformed by an exogenous DNA construct encoding the desired protein. "Synthetic" proteins are those prepared by chemical synthesis.

The term "related polynucleotides" means that regions or areas of the polynucleotides are identical and regions or areas of the polynucleotides are heterologous.

"Reductive reassortment", as used herein, refers to the increase in molecular diversity that is accrued through deletion (and/or insertion) events that are mediated by repeated sequences.

The following terms are used to describe the sequence relationships between two or more polynucleotides: "reference sequence," "comparison window," "sequence identity," "percentage of sequence identity," and "substantial identity."

A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

"Repetitive Index (RI)", as used herein, is the average number of copies of the quasi-repeated units contained in the cloning vector.

The term "saturation" refers to a technique of evolution wherein every possible change is made at each position of a template polynucleotide or template polypeptide; however the change at each position is not confirmed by testing, but merely assumed statistically wherein the majority of possible changes or nearly every possible change is estimated to occur at each position of a template. Saturation mutagenesis refers to mutating the DNA of a region of a gene encoding a protein that changes codon amino acid sequence of the protein and then screening the expressed mutants of essentially all of the mutants for an improved phenotype based on statistical over-sampling that approaches comprehensive coverage, but does not guarantee complete coverage.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

The term "silent mutation" refers to a codon change that does not result in an amino acid change in an expressed polypeptide and is based on redundancy of codon usage for amino acid insertion.

As known in the art "similarity" between two proteins is determined by comparing the amino acid sequence and its conserved amino acid substitutes of one protein to the sequence of a second protein. Similarity may be determined by procedures which are well-known in the art, for example, a BLAST program (Basic Local Alignment Search Tool at the National Center for Biological Information).

As used herein, the term "single-chain antibody" refers to a polypeptide comprising a VH domain and a VL domain in polypeptide linkage, generally liked via a spacer peptide (e.g., [Gly-Gly-Gly-Gly-Ser]$_x$), and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Specific hybridization" is defined herein as the formation of hybrids between a first polynucleotide and a second polynucleotide (e.g., a polynucleotide having a distinct but substantially identical sequence to the first polynucleotide), wherein substantially unrelated polynucleotide sequences do not form hybrids in the mixture.

The term "specific polynucleotide" means a polynucleotide having certain end points and having a certain nucleic acid sequence. Two polynucleotides wherein one polynucleotide has the identical sequence as a portion of the second polynucleotide but different ends comprises two different specific polynucleotides.

"Stringent hybridization conditions" means hybridization will occur only if there is at least 90% identity, preferably at least 95% identity and most preferably at least 97% identity between the sequences. See Sambrook et al., 1989, which is hereby incorporated by reference in its entirety.

Also included in the invention are polypeptides having sequences that are "substantially identical" to the sequence of a polypeptide, such as one of any SEQ ID NO disclosed herein. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure protein". The term "substantially pure protein" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

As used herein, "substantially pure" means an object species is the predominant species present (i.e., on a molar basis it is more abundant than any other individual macromolecular species in the composition), and preferably substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

DETAILED DESCRIPTION OF THE INVENTION

The disclosure provides a method for generation of enhanced full length antibodies in mammalian cells. A library of humanized variants is provided with high, validated framework diversity without requiring back-mutations to retain original affinity. No CDR grafting or phage display is required. In one embodiment, humanized antibody libraries are screened for antigen binding in ELISA compared to a donor antibody. In another embodiment, cell-based screening is used to determine biological activity. In another embodiment, the method comprises isotype switching compared to the donor antibody.

Antibodies are a class of serum proteins which are induced following contact with an antigen. They bind specifically to the antigen which induced their formation. Male, Immunology, Gower Medical Publishing, London, 1986, pp. 19-34 Immunoglobulin (Ig) is a synonym for antibody. Structurally, antibody molecules have a general four polypeptide chain structure consisting of two identical heavy chains (HC) and two identical light chains (LC), stabilized and cross-linked by intrachain and interchain disulfide bonds and noncovalent bonds. Heavy chains also have covalent carbohydrate portions. Different antibody classes consist of polymers of the four chain structure. Heavy chains are of 5 major types ($\gamma, \mu, \delta, \alpha, \epsilon$) and consist of 440-600 amino acid residues. Light chains are of two major types ($\kappa, \lambda$) and have about 220-230 amino acid residues. Both heavy and light chains are folded into domains. Proteolytic enzymes, such as papain and pepsin, can be used to split an antibody molecule into different characteristic fragments. Papain produces two separate and identical Fab fragments, each with one antigen-binding site, and one Fc fragment. Pepsin produces one $F(ab')_2$ fragment. Alberts et al., Molecular Biology of the Cell, 2nd ed., 1989, Garland Publishing, Inc.

Both light chains (LC) and heavy chains (HC) have a variable sequence at their amino-terminal ends but a constant sequence at their carboxyl-terminal ends. The light chains have a constant region about 110 amino acids long and a variable region of the same size. The heavy chains also have a variable region about 110 amino acids long, but the constant region of the H chains is about 330 or 440 amino acid long, depending on the class of the H chain. Alberts et al., Molecular Biology of the Cell, 2nd ed., 1989, Garland Publishing, Inc. at pp 1019. Only part of the variable region participates directly in the binding of antigen. Studies have shown that the variability in the variable regions of both L and H chains is for the most part restricted to three small hypervariable regions (also called complementarity-determining regions, or CDRs) in each chain. The remaining parts of the variable region, known as framework regions (FR), are relatively constant. Alberts et al., Molecular Biology of the Cell, 2nd ed., 1989, Garland Publishing, Inc. at pp 1019-1020.

In a preferred embodiment, the methods of the disclosure provide full length humanized antibody molecules, not Fabs or partial length fragments. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

Humanization by CDR Grafting Compared to Humanization Methods of the Disclosure

Humanization by CDR grafting, or reshaping, involves intercalating the mouse CDRs from each immunoglobulin chain within the FW regions of a human variable region.

One method of CDR grafting can be used to create what is called termed framework-patched immunoglobulins and is disclosed in Leung et al., U.S. Pat. No. 7,321,026, which is incorporated herein by reference. Unlike previous described methods of humanization, which grafted CDRs from a donor onto the frameworks of a single acceptor immunoglobulin, segments of framework (FR1, FR2, FR3, and FR4), or FRs, were patched to replace the corresponding FRs of the parent immunoglobulin. Free assortment of these FRs from different immunoglobulins and from different species was mixed and matched into forming the final immunoglobulin chain Immunoglobulin chains were prepared utilizing one or more complementarity determining regions (CDR's) from a donor immunoglobulin and portions of framework sequences from one or more human, or primate immunoglobulins. The individual FR sequences are selected by the best homology between the non-human antibody and the human antibody template. This approach, however, is labor intensive, and the optimal framework regions are not be easily identified.

Another method of CDR grafting is described by Williams et al. in Antibody Engineering, Vol. 1, Chapter 21, Konterman and Dubel, (eds.), Springer-Verlag Berlin Heidelberg 2010, pp. 319. FR sequences are selected by the best homology between the non-human antibody and the human antibody template. Selection of the human variable regions is considered to be of critical importance. There are over 9,000 heavy and over 2,500 kappa antibodies in the public databases. These include Kabat, GenBank, and IMGT databases. By aligning these databases with the Kabat numbering system and introducing gaps where necessary, each human variable region is scored for identity to the mouse sequence. The residue identity is determined at FW region, canonical, VH-VK interface residues and residues are identified from the homology models of potential importance. In addition, N-glycosylation patterns in the FW region are identified, which may lead to glycosylation-dependent effects on antibody binding. The resulting human variable region sequences are refined by maximizing sequence identity and homology to the mouse antibody.

The typical CDR grafting strategy described by Williams et al. 2010 starts with cloning and sequencing variable region cDNAs from a mouse B cell hydridoma. Chimeric heavy and light chain constructs are prepared utilizing the cDNA sequences. CDR grafted human variable regions are designed in parallel and CDR grafted humanized heavy and light chain constructs are prepared. Recombinant antibodies are expressed in transient transfection using chimeric and/or humanized expression constructs. The antigen binding potency of recombinant humanized antibodies is tested. If potency is low, further humanized antibody versions are prepared by substituting with selected framework mouse residues. The goal is to obtain a humanized antibody with optimum antigen binding potency, but with minimum mouse framework region antibodies. This process of humanization by CDR grafting is also somewhat labor intensive, potentially requiring multiple iterations to prepare a humanized antibody exhibiting the most desirable characteristics.

Another method of humanizing antibodies which also involves reshaping to reduce the immunogenicity involves synthesizing a combinatorial library comprising CDRs from a donor antibody fused in frame to framework regions from a sub-bank of framework regions. This technique, called framework-shuffling of antibodies, is disclosed in Wu et al US 2010/0216975, which is incorporated herein by reference. For example, Wu et al. prepared combinatorial sublibraries that were assembled sequentially using the polymerase chain reaction (PCR) by overlap extension.

The disclosure provides a technique of express humanization of antibodies with reduced immunogenicity; while maintaining or increasing antigen-binding specificity and affinity when compared to the donor antibody, and simultaneously optimizing protein expression. In one aspect, no additional affinity maturation is required.

The disclosure provides a method of producing humanized antibodies from a template antibody in which the variable region or CDRs are derived from the template antibody and the framework and constant regions of the antibody are derived from one or more human antibodies. In one aspect, the frameworks are from a human framework pool of functionally expressed human antibodies. In another aspect, a single sequence is utilized for framework region 4 in either or both of the light chain and the heavy chain. In a further aspect, the sequence encoding framework 4 is comprised in the expression vector. The variable region or CDRs derived from the template antibody preferably have from about 90% to about 100% identity with the variable region or CDRs of the template antibody, although any and all modifications, including substitutions, insertions and deletions, are contemplated so long as the humanized antibody maintains the ability to bind to the target antigen.

The regions of the humanized antibodies that are derived from human antibodies need not have 100% identity with the human antibodies. In a preferred embodiment, as many of the human amino acid residues as possible are retained in order that immunogenicity is negligible, but the human residues, in particular residues of the framework region, are substituted as required and as taught herein below in accordance with the present invention. Such modifications as disclosed herein are necessary to support the antigen binding site formed by the CDRs while simultaneously maximizing the humanization of the antibody. In one specific aspect, the framework regions of the humanized antibodies that are derived from the human framework pool have 100% identity with the human antibodies.

Each of the heavy and light chain variable regions contain three CDRs that combine to form the antigen binding site. The three CDRs are surrounded by four FR regions that primarily function to support the CDRs. The sequences of the CDRs within the sequences of the variable regions of the heavy and light chains can be identified by computer-assisted alignment according to Kabat et al. (1987) in Sequences of Proteins of Immunological Interest, 4$^{th}$ ed., United States Department of Health and Human Services, U.S. Government Printing Office, Washington, D.C., or by molecular modeling of the variable regions, for example utilizing the ENCAD program as described by Levitt (1983) J. Mol. Biol. 168:595.

In one embodiment the CDRs are derived from one or more template antibodies. Determination of the heavy chain CDRs and light chain CDRs is well within the skill of one in the art. See, for example, http://www.bioinf.org.uk/abs/.

The sequences of the CDRs of the humanized antibody may be modified or evolved by any technique known in the art and may include insertions, substitutions and deletions to the extent that the humanized antibody maintains the ability to bind to and the target antigen. The ordinarily skilled artisan can ascertain the maintenance of this activity by performing the functional assays described herein below.

The humanized HC variable domain encoding library derived from one or more of the CDRs of the template antigen and humanized LC variable domain encoding library derived from one or more of the CDRs of the template antigen may be combined with the human constant and framework regions to form the humanized antibody. Human genes which encode the constant (C) regions of the humanized antibodies, fragments and regions of the present invention can be derived from a human fetal liver library, by known methods. Human C region genes can be derived from any human cell including those which express and produce human immunoglobulins. The human $C_H$ region can be derived from any of the known classes or isotypes of human H chains, including γ, μ, α, δ, ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1).

The human $C_L$ region can be derived from either human L chain isotype, kappa or lambda, preferably kappa.

Genes encoding human immunoglobulin C regions are obtained from human cells by standard cloning techniques (Sambrook, et al. (Molecular Cloning: A Laboratory Manual, 2$^{nd}$ Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof. Chimeric antibody fragments, such as F(ab$^1$)$_2$ and Fab, can be prepared by designing a chimeric H chain gene which is appropriately truncated. For example, a chimeric gene encoding an H chain portion of an F(ab$^1$)$_2$ fragment would include DNA sequences encoding the CH1 domain and hinge region of the H chain, followed by a translational stop codon to yield the truncated molecule.

Generally, in one example, humanized antibodies, fragments and regions of the present invention are produced by cloning DNA segments encoding the H and L chain antigen-binding regions comprising one or more CDRs of the template antibody, and joining these DNA segments to DNA segments including $C_H$ and $C_L$ regions, respectively, to produce full length chimeric immunoglobulin-encoding genes.

The sequences of the variable regions of the antibody may be modified by insertions, substitutions and deletions to the extent that the chimeric antibody maintains the ability to bind to and inhibit the target antigen. The ordinarily skilled artisan can ascertain the maintenance of this activity by performing appropriate functional assays.

Methods for engineering or humanizing non-human or human antibodies can be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman com/immunology/CH05/kuby05.htm; www.library.thinkquest.org/12429/Immune/Antibody.html; www.hhmi.org/grants/ lectures/1996/vlab/; www.path.cam.ac.uk/.about.mrc7/mikeimages.html; www.antibodyresource.com/; mcb.harvard.edu/BioLinks/Immunology.html.www.immunologylink.com/; pathbox.wust1.edu/.about.hcenter/index.html; www.biotech.ufl.edu/.about.hcl/; www.pebio.com/pa/340913/340913.html; www.nal.usda.gov/awic/pubs/antibody/; www.m.ehime-u.ac.jp/.about.yasuhito/Elisa.html; www.biodesign.com/table.asp; www.icnet.uk/axp/facs/davies/links.html; www.biotech.ufl.edu/.about.fccl/protocol.html; www.isac-net.org/sites-geo.html; aximt1.imt.uni-marburg.de/.about.rek/AEP-Start.html; baserv.uci.kun.nl/.about.jraats/links1.html; www.recab.uni-hd.de/immuno.bme.nwvu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.aboutimolina/Web-pages/Pept/spottech.html; www.jerini.de/fr_products.htm; www.patents.ibm.con/ibm.html. Kabat et al. Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The human constant region of the humanized antibody of the invention can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the humanized human antibody comprises an IgG1 heavy chain and a IgG1light chain. The isolated humanized antibodies of the present invention comprise antibody amino acid sequences disclosed herein encoded by any suitable polynucleotide as well as. Preferably, the humanized antibody binds the target antibody and, thereby partially or substantially neutralizes at least one biological activity of the protein.

In one aspect, the humanized antibody will comprise an antigen-binding region that comprises at least one human complementarity determining region (CDR1, CDR2 and CDR3) or variant of at least one heavy chain variable region and at least one human complementarity determining region (CDR4, CDR5 and CDR6) or variant of at least one light chain variable region, derived from the template antibody.

In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3. In another particular embodiment, the antibody or antigen-binding portion or variant can have an antigen-binding region that comprises at least a portion of at least one light chain CDR (i.e., CDR4, CDR5 and/or CDR6) having the amino acid sequence of the corresponding CDRs 4, 5 and/or 6. In one embodiment the three heavy chain CDRs and the three light chain CDRs of the antibody or antigen-binding fragment have the amino acid sequence of the corresponding CDR of the template antibody. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method and using any of the possible redundant codons that will result in expression of a polypeptide of the invention.

In another embodiment, the disclosure provides a method of humanization of antibodies that comprises expression of a full length antibody in a eukaryotic cell production host; the method comprising selecting a template antibody; evolving one or more CDR sequences from the template antibody to produce one or more CDR fragment libraries; ligating the CDR fragment libraries with a human framework pool from functionally expressed antibodies, wherein a single sequence for each framework region 4 is utilized from the pool; screening the variant antibodies for at least one predetermined property, characteristic or activity; selecting a variant humanized antibody from the set of mutant antibodies based upon reduction of immunogenicity, and affinity for the antigen, compared to the template antibody. In one aspect, one or more of the variant humanized antibodies are optimized for at least one additional predetermined property, characteristic or activity compared to the template antibody; such as expression level; and the antibodies are expressed in the same eukaryotic cell production host as in the evolving step for any commercial scale. In one aspect, the humanized antibody is selected from the library of humanized antibodies based upon (1) reduced immunogenicity compared to the template antibody; (2) optimization of the at least one predetermined antigen binding property, characteristic or activity compared to the template antibody; and (3) a high level of expression when compared to other humanized antibodies in the library.

In one embodiment, the method of the disclosure comprises selection of a template antibody that is directed to a specific antigen of interest. The template antibody may be an existing murine monoclonal antibody, or a chimeric antibody, or even an existing humanized antibody for which one or more characteristics is desired to be improved or optimized.

In one aspect, the template antibody is cloned and sequenced to identify sequences for FW1, CDR1, FW2, CDR2, FW3, CDR3, and optionally FW4 of the immunoglobulin variable portions of both the heavy chain and the light chain.

Fragment libraries of ds DNA encoding variants of one or more of HC CDR1, HC CDR2, HC CDR3, LC CDR1, LC CDR2 and LC CDR3 derived by any method of evolution from the template antibody are prepared by any means known in the art. Specifically, the double stranded DNA fragment libraries comprise complementarity determining region (CDR) fragment encoding libraries including fragments encoding all or a portion of one or more of HC CDR1, HC CDR2, HC CDR3, LC CDR1, LC CDR2 and LC CDR3 derived from the template antibody. In one aspect, the libraries for one, two, three, four, or five of the HC CDR1, HC CDR2, HC CDR3, LC CDR1, LC CDR2 and LC CDR3 may contain a single member comprising the sequence of the corresponding region on the template antibody.

In another aspect, the evolving step comprises an evolution technique. Any method of evolution is performed on the nucleic acid sequence encoding the template antibody, or a fragment thereof, such as a CDR fragment, to prepare an antibody or fragment library. In one aspect, the evolution is performed by a method of comprehensive protein engineering to ultimately produce the set of mutant antibodies. The method of comprehensive protein engineering can be selected, for example, from one or a combination of Comprehensive Positional Evolution (CPE™), Comprehensive Protein Synthesis (CPS™) Flex Evolution, Synergy Evolution, Comprehensive Positional Insertion evolution (CPI™) or Comprehensive Positional Deletion evolution (CPD™). These techniques are disclosed in detail in PCT/US2010/42302, filed Jul. 16, 2010, and incorporated herein by reference. In another aspect, the mutant antibodies are expressed in the same mammalian system used to generate the human antibody library.

In another embodiment, a template hybridoma or recombinant antibody is selected for a particular target antigen; evolution of one or more CDRs of the template antibody is performed to ultimately provide a set of mutant antibodies which are screened, for example, by use of antibody cell surface display in a mammalian cell system; and manufacturing is performed in the same mammalian cell system used for screening.

In another embodiment, the selected template hybridoma/recombinant antibody is humanized and screened in the manufacturing host, followed by production in the manufacturing host, wherein the step of optimization (evolution) is omitted altogether.

In other aspects of the present invention, downstream expression optimization in manufacturing hosts is performed by evolving the Fc region of the antibody, silent codons in the antibody, and/or the vector and/or host genes used in protein expression. In one aspect, an Fc library is generated by any evolutionary technique. In one specific aspect of expression optimization, comprehensive evolution is performed on Fc domain of an antibody to create a library of Fc mutants which can be used to select an optimal partner for any Fv. Optimization is designed for rapid attachment of all Fc variants to each new Fv region. Alternatively, a subset of these Fcs can be used to attach to different Fvs. Each of these Fc variant/Fv combinations is screened as a full-length antibody expressed in mammalian cells (e.g. CHO, cost-effective media) for optimal expression. Further, CPS can be performed to screen all theoretical permutations of up to 12 or more of these CPE hits in mammalian cells for expression improvement. Specific desirable codon changes can also be selected to identify clones with increased expression. Silent codons are identified and CPE is performed on these positions. This CPE library is screened to identify optimal expression hits. Further, all theoretical permutations of up to 12 or more CPE hits can be used in the CPS process to generate a new library that can be screened in mammalian cells for expression improvement. The top CPS silent mutation hits are used to customize protein for optimal expression in a specific cell line and media. This provides opportunity for biosimilar fine structure control.

Other areas for enhancement of expression include: optimization of the vector, including promoter, splice sites, 5' and 3' termini, flanking sequences, reduction of gene deletion and rearrangement, improvement of host cell gene activities, optimization of host glycosylating enzymes, and chromosome wide host cell mutagenesis and selection. It has been demonstrated that 5' amino acid sequences are important for enhancement of expression.

Evolution of Lead Candidates

In another aspect, any method of protein evolution can be employed for simultaneous evolution of antibody performance and expression optimization. Optimization of protein performance can include improvement of various characteristics such as affinity, pharmacokinetic characteristics, tissue targeting, protein-protein aggregation, addressing high assay variability and modifying other in vivo characteristics.

Methods for evolving molecules, including template antibodies of the present invention, include stochastic and non-stochastic methods. Published methods include random and non-random mutagenesis approaches. Any of these approaches can be employed to further evolve properties of the humanized antibodies of the disclosure toward a desired characteristic, such as better stability in different temperature or pH environments, or better expression in a host cell. Other potentially desirable properties, such as improved catalytic activity, improved protein stability in various conditions, improved selectivity and/or solubility, and improved expression results by improvement of characteristics such as reduced aggregation can be selected for in evolution experiments.

Evolution can be performed directly in a eukaryotic host, such as a mammalian cell host or a yeast cell host, that will be used for downstream production of the therapeutic protein. Candidates can be evolved for optimal expression in the same host used to screen and/or evolve and to manufacture. Expression optimization can be achieved by optimization of vectors used (vector components, such as promoters, splice sites, 5' and 3' termini and flanking sequences), gene modification of host cells to reduce gene deletions and rearrangements, evolution of host cell gene activities by in vivo or in vitro methods of evolving relevant genes, optimization of host glycosylating enzymes by evolution of relevant genes, and/or by chromosome wide host cell mutagenesis and selection strategies to select for cells with enhanced expression capabilities. Host cells are further described herein.

Cell surface display expression and screening technology (for example, as defined above) can be employed to screen libraries of evolved proteins for candidates to be manufactured.

Current methods in widespread use for creating alternative proteins from a starting molecule are oligonucleotide-directed mutagenesis technologies, error-prone polymerase chain reactions and cassette mutagenesis, in which the specific region to be optimized is replaced with a synthetically mutagenized oligonucleotide. In these cases, a number of mutant sites are generated around certain sites in the original sequence.

In oligonucleotide-directed mutagenesis, a short sequence is replaced with a synthetically mutagenized oligonucleotide. Error-prone PCR uses low-fidelity polymerization conditions to introduce a low level of point mutations randomly over a long sequence. In a mixture of fragments of unknown sequence, error-prone PCR can be used to mutagenize the mixture. In cassette mutagenesis, a sequence block of a single template is typically replaced by a (partially) randomized sequence.

Chimeric genes have been made by joining 2 polynucleotide fragments using compatible sticky ends generated by restriction enzyme(s), where each fragment is derived from a separate progenitor (or parental) molecule. Another example is the mutagenesis of a single codon position (i.e. to achieve a codon substitution, addition, or deletion) in a parental polynucleotide to generate a single progeny polynucleotide encoding for a single site-mutagenized polypeptide.

Further, in vivo site specific recombination systems have been utilized to generate hybrids of genes, as well as random methods of in vivo recombination, and recombination between homologous but truncated genes on a plasmid. Mutagenesis has also been reported by overlapping extension and PCR.

Non-random methods have been used to achieve larger numbers of point mutations and/or chimerizations, for example comprehensive or exhaustive approaches have been used to generate all the molecular species within a particular grouping of mutations, for attributing functionality to specific structural groups in a template molecule (e.g. a specific single amino acid position or a sequence comprised of two or more amino acids positions), and for categorizing and comparing specific grouping of mutations. U.S. Pat. No. 7,033,781 entitled "Whole cell engineering my mutagenizing a substantial portion of a starting genome, combining mutations, and optionally repeating" describes a method of evolving an organism toward desired characteristics. U.S. Pat. No. 6,764,835 entitled "Saturation mutagenesis in directed evolution" and U.S. Pat. No. 6,562,594 entitled "Synthetic ligation reassembly in directed evolution" describe methods of exhaustively evolving and screening for desired characteristics of molecules. Any such methods can be used in the method of the present invention.

There is a difference between previously known methods of "saturation mutagenesis" and techniques of "comprehensive" evolution preferred herein. Saturation mutagenesis refers to a technique of evolution wherein every possible change is made at each position of a template polynucleotide or template polypeptide; however the change at each position is not confirmed by testing, but merely assumed statistically. Comprehensive evolution refers to a technique of evolution wherein every possible change is made at each position of a template polynucleotide or template polypeptide and the polynucleotide or polypeptide is tested to confirm the intended change has been made.

In another embodiment, the CPE/EvoMap may be used to identify and exploit fully mutable sites. In one aspect, exploitation of multiple fully mutable sites is termed Flex Evolution and is used to make targeted changes such as introduction of sites for glycosylation (e.g. codons for amino acids for N- or O-linked glycosylation; Asn within consensus sequence Asn-Aa-Ser-Thr or Ser/Thr) and chemical conjugation. Flex evolution may also be used in design of protease cleavage sites, introduction of tags for purification and/or detection, site-specific labeling, and the like. Further, codon optimization of silent mutations may be utilized for improvement of protein expression. In this embodiment, termed Flex Evolution, following protein expression, the mutant polypeptide libraries produced are rescreened for at least one predetermined property, characteristic or activity compared to the template polypeptide. In one aspect, the predetermined property includes reduction of protein-protein aggregation, enhancement of protein stability, or increased protein solubility. In one aspect, the mutant polypeptide libraries are screened for two or more properties simultaneously. In another aspect, any eukaryotic expression system which glycosylates may be used for the introduction of glycosylation sites, such as, for example, mammalian, plant, yeast, and insect cell lines.

In the technique of Flex Evolution, evaluation of bioinformatics and protein x-ray crystal structures of related proteins, or the template protein or polypeptide, is useful for template optimization. In one aspect, selected sites are not at contact residues. In another aspect, selection of non-surface protein mutations allows for reduced immunogenicity risk.

Applications of Flex Evolution include, bit are not limited to, reduction of protein-protein aggregation, improvement of protein solubility, optimization of pharmacokinetics via glycosylation libraries, optimization of protein secondary and tertiary structure and deimmunization of antigenic sites directly via either mutation sets or indirectly through glycosylation masking.

In one aspect of Flex Evolution, an EvoMap™ is utilized to identify fully mutable sites, CPS generation is performed with insertion of glycosylating residues to fully mutable sites (or silent mutations for translation effects), and screening of combinatorial glycosylated library is performed by analytical analysis (e.g. Mass Spectroscopy analysis, Dynamic Light Scattering), immunogenicity reduction (by bioinformatics or assay), and/or pharmacokinetic analysis (e.g. in Foxn1nu mice).

In one aspect, Flex evolution may be used for deimmunization to eliminate immunogenicity while maintaining function. Flex Evolution deimmunization can be performed by masking immunogenicity with glycosylation, identifying human hypersomatic mutation spectra amino acid substitutions that may eliminate immunogenicity while maintaining function, reduction of dose for evading immunogenicity potential, and minimization of non-surface amino acid residue changes. Further, immunogenicity databases and algorithms can be used to identify and replace potential MHC binding epitopes. In one aspect, in silico modification prediction is coupled with CPE/CPS data to generate variants.

Reduced propensity to generate T-cell epitopes and/or deimmunization may be measured by techniques known in the art. Preferably, deimmunization of proteins may be tested in vitro by T cell proliferation assay. In this assay PBMCs from donors representing >80% of HLA-DR alleles in the world are screened for proliferation in response to either wild type or deimmunized peptides. Ideally cell proliferation is only detected upon loading of the antigen-presenting cells with wild type peptides. Additional assays for deimmunization include human in vitro PBMC re-stimulation assays (e.g. interferon gamma (TH1) or IL4 (TH2) ELISA. Alternatively, one may test deimmunization by expressing HLA-DR tetramers representing all haplotypes. In order to test if de-immunized peptides are presented on HLA-DR haplotypes, binding of e.g. fluorescence-labeled peptides on PBMCs can be measured. Measurement of HLA Class I and Class II transgenic mice for responses to target antigen (e.g. interferon gamma or IL4). Alternatively epitope library screening with educated T cells (MHCI 9mer; MHCII 20mer) from PBMC and/or transgenic mouse assays. Furthermore, deimmunization can be proven by determining whether antibodies against the deimmunized molecules have been generated after administration in patients.

In one aspect, the present invention discloses the utilization of protein engineering methods to develop silent mutation codon optimized Fc variants with improved expression in eukaryotic cells. A silent mutation is one in which the variation of the DNA sequence does not result in a change in the amino acid sequence of the preotein. In one aspect, codon mutagenesis is performed in the constant region for optimization of eukaryotic cell expression. A codon optimized Fc variant with improved expression properties while retaining the capacity to mediate effector functions improves the production of therapeutic antibodies. In this aspect, for example, a constant region of an antibody molecule can be evolved for screening in different expression hosts, for example, mammalian cell lines expression screening utilizing CHO, HEK293 and COS-7.

Comprehensive Positional Insertion Evolution

In one embodiment, the disclosure provides methods of identifying and mapping mutant polypeptides formed from, or based upon, a template antibody. Using a linear peptide as a simple example, in a first step, a set of naturally occurring amino acid variants (or a subset thereof, or amino acid derivatives) for each codon from position 2 to n (n corresponding to the number of residues in the polypeptide chain) is generated by a process referred to herein as Comprehensive Positional Insertion (CPI™) evolution.

In CPI™, an amino acid is inserted after each amino acid throughout a template polypeptide one at a time to generate a set of lengthened polypeptides. CPI can be used to insert 1, 2, 3, 4, or up to 5 new sites at a time. Each of the 20 amino acids is added at each new position, one at a time, creating a set of 20 different molecules at each new position added in the template. In this case, position 1, which is methionine and invariant, is skipped. This procedure is repeated for each polypeptide chain of the target molecule. A minimum set of amino acid mutations contains only one codon for each of the 20 natural amino acids.

The present invention relates to methods of identifying and mapping mutant polypeptides formed from, or based upon, a template polypeptide. Typically, the polypeptide will comprise n amino acid residues, wherein the method comprises (a) generating n+[20×(n−1)] separate polypeptides, wherein each polypeptide differs from the template polypeptide in that it has inserted after each position in the template each of the 20 amino acids one at a time; assaying each polypeptide for at least one predetermined property, characteristic or activity; and (b) for each member identifying any change in said property, characteristic or activity relative to the template polypeptide.

In one embodiment, one or more regions are selected for mutagenesis to add one position at a time as described above. In such case, n represents a subset or region of the template polypeptide. For example, where the polypeptide is an antibody, the entire antibody or one or more complementarity determining regions (CDRs) of the antibody are subjected to mutagenesis to add one position at a time in the template polypeptide after each position.

The invention thus includes methods of mapping a set of mutant antibodies formed from a template antibody having at least one, and preferably six, complementarity determining regions (CDRs), the CDRs together comprising n amino acid residues, the method comprising (a) generating n+[20×(n−1)] separate antibodies, wherein each antibody differs from the template antibody in that has inserted a single predetermined position, one at a time, after each position in the template sequence; (b) assaying each set for at least one predetermined property, characteristic or activity; and (c) for each member identifying any change in a property, characteristic or activity relative to the template polypeptide. For antibodies, the predetermined property, characteristic or property may be binding affinity and/or immunogenicity, for example.

In addition, provided are methods of producing a set of mutant antibodies formed from a template antibody having at least one complementarity determining region (CDR), the CDR comprising n amino acid residues, the method comprising: (a) generating n+[20×(n−1)] separate antibodies, wherein each antibody differs from the template antibody in that it has an extra amino acid added at a single predetermined position of the CDR. In another embodiment, the antibody comprises six CDRs, and together the CDRs comprise n amino acid residues.

In another embodiment, the new lengthened polypeptides described above are further mutated and mapped after screening to identify a change in a property, characteristic or activity relative to the shortened polypeptide. Typically, the lengthened polypeptide will comprise n amino acid residues, wherein the method comprises (a) generating n (n−1 in the case where the initial residue is methionine) separate sets of polypeptides, each set comprising member polypeptides having X number of different predetermined amino acid residues at a single predetermined position of the polypeptide; wherein each set of polypeptides differs in the single predetermined position; assaying each set for at least one predetermined property, characteristic or activity; (b) for each member identifying any change in said property, characteristic or activity relative to the template polypeptide; and optionally (c) creating a functional map reflecting such changes. Preferably, the number of different member polypeptides generated is equivalent to n×X (or [n−1]×X, as the case may be).

In the alternative, the method comprises generating a single population comprising the sets of mutated polypeptides from the lengthened polypeptides. In this embodiment, the entire new population is screened, the individual members identified, and the functional map generated.

Typically, where each naturally occurring amino acid is used, X will be 19 (representing the 20 naturally occurring amino acid residues and excluding the particular residue present in a given position of the template polypeptide). However, any subset of amino acids may be used throughout, and each set of polypeptides may be substituted with all or a subset of the total X used for the entire population.

However, it is recognized that each expression system may suffer from codon bias, in which insufficient tRNA pools can lead to translation stalling, premature translation termination, translation frameshifting and amino acid misincorporation. Therefore, for expression optimization each set contains up to 63 different codons.

Each amino acid set is then screened for at least one, and preferably two or more, desirable characteristic such as improved function; neutral mutations, inhibitory mutations, and expression.

In one aspect, the lengthened polypeptides can be mapped to identify a change in a property, characteristic or activity resulting in the shortened polypeptides relative to the "wild-type". The data for each set are combined for the entire polypeptide, or "target molecule". Hits from the screening of the lengthened polypeptides (target molecules) can then be used for further comprehensive mutagenesis chain(s) and screening as described herein. The data from mutagenesis provides a detailed functional map (referred to herein as an EvoMap™) of the target molecule is generated. This map contains detailed information how each mutation affects the performance/expression of the target molecule. It allows for the identification of all sites where no changes can be made without a loss in protein function (or antigen/receptor binding in case of antibodies). It also shows where changes can be made without affecting function.

In another aspect, CPE can be used to generate a library of 5, 10, up to 15, or up to all 19 amino acids at each position of interest.

Comprehensive Positional Deletion Evolution

Comprehensive Positional Deletion Evolution (CPD™) relates to methods of identifying and mapping mutant polypeptides formed from, or based upon, a template polypeptide. CPD evolution deletes every amino acid through the protein one position at a time. Typically, the polypeptide will comprise n amino acid residues, wherein the method comprises (a) generating n−1 (n−2 in the case where the initial residue is methionine) separate polypeptides, wherein each polypeptide differs from the template polypeptide in that it lacks a single predetermined position; assaying each polypeptide for at least one predetermined property, characteristic or activity; and (b) for each member identifying any change in said property, characteristic or activity relative to the template polypeptide.

In one embodiment of CPD evolution, one or more regions are selected for mutagenesis to remove one position at a time. In such case, n represents a subset or region of the template polypeptide. For example, where the polypeptide is an antibody, the entire antibody or one or more complementarity determining regions (CDRs) of the antibody are subjected to mutagenesis to remove one position at a time in the template polypeptide.

In one embodiment, CPD thus includes methods of mapping a set of mutant antibodies formed from a template antibody having at least one, and preferably six, complementarity determining regions (CDRs), the CDRs together comprising n amino acid residues, the method comprising (a) generating (n−1) separate antibodies, wherein each antibody differs from the template antibody in that lacks a single predetermined position; (b) assaying each set for at least one predetermined property, characteristic or activity; and (c) for each member identifying any change in a property, characteristic or activity relative to the template polypeptide. For antibodies, the predetermined property, characteristic or property may be binding affinity and/or immunogenicity, for example.

One aspect of CPD evolution includes methods of producing a set of mutant antibodies formed from a template antibody having at least one complementarity determining region (CDR), the CDR comprising n amino acid residues, the method comprising: (a) generating n−1 separate antibodies, wherein each antibody differs from the template antibody in that lacks a single predetermined position of the CDR. In another embodiment, the antibody comprises six CDRs, and together the CDRs comprise n amino acid residues.

In another embodiment of CPD evolution, the new shortened polypeptides described above are further mutated and mapped after screening to identify a change in a property, characteristic or activity relative to the shortened polypeptide. Typically, the shortened polypeptide will comprise n amino acid residues, wherein the method comprises (a) generating n (n−1 in the case where the initial residue is methionine) separate sets of polypeptides, each set comprising member polypeptides having X number of different predetermined amino acid residues at a single predetermined position of the polypeptide; wherein each set of polypeptides differs in the single predetermined position; assaying each set for at least one predetermined property, characteristic or activity; (b) for each member identifying any change in said property, characteristic or activity relative to the template polypeptide; and (c) creating a functional map reflecting such changes. Preferably, the number of different member polypeptides generated is equivalent to n×X (or [n−1]×X, as the case may be).

In the alternative, the CPD method comprises generating a single population comprising the sets of mutated polypeptides from the shortened polypeptides. In this embodiment, the entire new population is screened, the individual members identified, and the functional map generated. Typically, where each naturally occurring amino acid is used, X will be 19 (representing the 20 naturally occurring amino acid residues and excluding the particular residue present in a given position of the template polypeptide). However, any subset of amino acids may be used throughout, and each set of polypeptides may be substituted with all or a subset of the total X used for the entire population.

Any mutational or synthetic means may be used to generate the set of mutants in CPD evolution. In one embodiment, the generation of polypeptides comprises (i) subjecting a codon-containing polynucleotide encoding for the template polypeptide to polymerase-based amplification using a 64-fold degenerate oligonucleotide for each codon to be mutagenized, wherein each of the 64-fold degenerate oligonucleotides is comprised of a first homologous sequence and a degenerate N,N,N triplet sequence, so as to generate a set of progeny polynucleotides; and (ii) subjecting the set of progeny polynucleotides to clonal amplification such that polypeptides encoded by the progeny polynucleotides are expressed.

In one embodiment of CPD evolution, the entire shortened polypeptide is subjected to saturation mutagenesis. In another embodiment, one or more regions are selected for saturation mutagenesis. In such case, n represents a subset or region of the template polypeptide. For example, where the polypeptide is an antibody, the entire antibody or one or more complementarity determining regions (CDRs) of the antibody are subjected to saturation mutagenesis.

The CPD evolution disclosure thus includes methods of mapping a set of mutant antibodies formed from a shortened template antibody having at least one, and preferably six, complementarity determining regions (CDRs), the CDRs together comprising n amino acid residues, the method comprising (a) generating n separate sets of antibodies, each set comprising member antibodies having X number of different predetermined amino acid residues at a single predetermined position of the CDR; wherein each set of antibodies differs in the single predetermined position; and the number of different member antibodies generated is equivalent to n×X; (b) assaying each set for at least one predetermined property, characteristic or activity; (c) for each member identifying any change in a property, characteristic or activity relative to the template polypeptide; and (d) creating a structural positional map of such changes. For antibodies, the predetermined property, characteristic or property may be binding affinity and/or immunogenicity. As set forth above, in the alternative a single population comprising all sets of mutated antibodies may be generated.

In addition, provided are methods of producing a set of mutant antibodies formed from a shortened template antibody having at least one complementarity determining region (CDR), the CDR comprising n amino acid residues, the method comprising: (a) generating n separate sets of antibodies, each set comprising member antibodies having X number of different predetermined amino acid residues at a single predetermined position of the CDR; wherein each set of antibodies differs in the single predetermined position; and the number of different member antibodies generated is equivalent to n×X. In another embodiment, antibody comprises six CDRs, and together the CDRs comprise n amino acid residues.

Combinatorial Protein Synthesis

Combinatorial Protein Synthesis (CPS™) involves combining individual hits from any evolutionary technique to combine two or more mutations.

Nucleic Acid Molecules

Using the information provided herein, such as the nucleotide sequences encoding at least 70-100% of at least one of the contiguous CDR amino acid sequences from the template antibody or specified fragments, variants or consensus sequences thereof, or a deposited vector comprising at least one of these sequences, a nucleic acid molecule of the present invention encoding at least one anti-antigen antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. In one embodiment, the DNA is double stranded. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules comprising the coding sequence for a template antibody or variable region and nucleic acid molecules which comprise a nucleotide sequence encoding a variant of the template antibody. Of course, the genetic code is well known in the art. Thus, it would be routine for one skilled in the art to generate such degenerate nucleic acid variants that code for specific antiantigen, for example, humanized antibodies of the present invention. See, e.g., Ausubel, et al., supra, and such nucleic acid variants are included in the present invention. Nonlimiting examples of isolated nucleic acid molecules of the present invention include nucleic acid fragments encoding, respectively, all or a portion of HC CDR1, HC CDR2, HC CDR3, LC CDR1, LC CDR2, LC CDR3, HC variable region and LC variable regions.

As indicated herein, nucleic acid molecules prepared by the methods of the disclosure which comprise a nucleic acid encoding a variant of a template antibody can include, but are not limited to, those encoding the amino acid sequence of an antibody fragment, by itself, the coding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Prior methods of designed protein libraries include the technique of Gene Assembly Mutagenesis. Whole genes and plasmids can be assembled from relatively short, synthetic, overlapping oligodeoxyribonucleotides (oligos) by DNA polymerase extension. Gene Assembly mutagenesis achieves a population of gene variants assembled from short single stranded oligonucleotides encoding both strands of the gene and containing degenerate bases at the targeted positions. Following assembly PCR the full length gene variants are amplified using outside primers. The assembly mutagenesis method has a technical limitation of introducing non-targeted mutations at an elevated rate relative to routine PCR. While the extra diversity can be an advantage, it might be necessary to increase the library size to ensure complete representation of all possible intended sequences. See for example, Bassette et al., 2003, Construction of Designed Protein Libraries Using Gene Assembly Mutagenesis. Directed Evolution Library Creation, Methods and protocols. Edit by Frances H. Arnold and George Georgiou, Methods in Molecular Biology, 231, 29-37.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Framework fragment encoding libraries of dsDNA which encode for all or a portion of HC FW1, HC FW2, HC FW3, LC FW1, LC FW2, and LC FW3 regions are selected from a human framework pool selected only from functionally expressed antibodies from human germline sequences. The human framework pool is selected for maximum sequence diversity.

The method of the disclosure further comprises the step of assembling from the HC fragment libraries by stepwise liquid phase ligation of heavy chain FW encoding fragments and CDR encoding fragments in the order of: FW1-CDR1-FW2-CDR2-FW3-CDR3 to produce a humanized HC variable domain encoding library.

The method of the disclosure further comprises the step of assembling from the LC fragment libraries by stepwise liquid phase ligation of light chain FW encoding fragments and CDR encoding fragments in the order of: FW1-CDR1-FW2-CDR2-FW3-CDR3 to produce a humanized LC variable domain encoding library.

Liquid phase synthesis of combinatorial variable domain humanized libraries for the light chain and the heavy chain can be employed. The assembly of a humanized light chain (LC) variable domain library, for example, contains human light chain frameworks (FW) and non-human complementarity determining regions (CDR). The library is assembled by, for example, by using stepwise liquid phase ligation of FW and CDR DNA fragments. The libraries are assembled by using stepwise liquid phase ligation of FW and CDR DNA fragments in the order of FW1-CDR1-FW2-CDR2-FW3-CDR3 by techniques known to one of skill in the art. For example, by the techniques of one or more of the following references, each of which is incorporated herein by reference. Lo, B. K., 2003, Antibody humanization by CDR grafting. Antibody Engineering, Methods and protocols. Edit by Benny K. C. Lo, Methods in Molecular Biology, 248, 135-159; Kashmiri et al., 2003, Developing a minimally immunogenic humanized antibody by SDR grafting. Antibody Engineering, Methods and protocols. Edit by Benny K. C. Lo, Methods in Molecular Biology, 248, 361-376; Bassette, P. H., et al., 2003, Construction of Designed Protein Libraries Using Gene Assembly Mutagenesis. Directed Evolution Library Creation, Methods and protocols. Edit. Arnold and Georgiou, Methods in Molecular Biology, 231, 29-37; Chames, P., et al., 2001, Selections on Biotinylated antigens. Antibody Engineering, Edit by R. Kontermann and S. Dubel, Springer Lab Manual, 149-166; O'Brien S., and Jones, T., 2001, Humanising antibodies by CDR grafting. Antibody Engineering, Edit by R. Kontermann and S. Dubel, Springer Lab Manual, 567-590. Assembly of fragments is further described in detail herein.

As stated, the invention also relates to a method of producing full length humanized antibodies, comprising one or more CDRs derived from a template antibody and framework regions from a human framework pool with frameworks only from functionally expresses antibodies. The human framework pool is selected to provide maximum framework sequence diversity. Such humanized antibodies can include one or more amino acid substitutions, deletions or additions, either from natural mutations or human manipulation, as specified herein. Preferably, such antibodies can bind the antigen with high affinity (e.g., $K_D$ less than or equal to about $10^{-9}$ M) Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given humanized antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-antigen antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one antigen neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

The method of the disclosure also comprises the step of cloning the assembled humanized heavy chain variable domain library and the assembled light chain variable domain library into an expression vector to create a humanization library. In one aspect, the expression vector comprises a nucleotide sequence encoding framework region 4. The humanization library is transfected into cells.

Vectors and Host Cells

The present invention also relates to vectors that include isolated nucleic acid molecules of the present invention, host cells that are genetically engineered with the recombinant vectors, and the production of at least one humanized antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Cloning and Expression of Humanized Antibodies in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NS0 cells are often used for the production of antibodies.

Cloning and Expression in CHO Cells

In one aspect, the isolated variable and constant region encoding DNA and the dephosphorylated vector are ligated with T4 DNA ligase. E. coli HB101 or XL-1 Blue cells are then transformed and bacteria are identified that contain the fragment inserted into plasmid pC4 using, for instance, restriction enzyme analysis.

For example, in one aspect, Chinese hamster ovary (CHO) cells lacking an active DHFR gene are used for transfection. 5 µg of the expression plasmid pC4 is cotransfected with 0.5 µg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 µg/ml G418. After 2 days, the cells are trypsinized and seeded in hybridoma cloning plates (Greiner, Germany) in alpha minus MEM supplemented with 10, 25, or 50 ng/ml of methotrexate plus 1 µg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot, ELISA, or by reverse phase HPLC analysis.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art. In one aspect, the cells are selected from a eukaryotic cell production host cell line selected from a member of the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells, including COS-1 (e.g., ATCC CRL 1650), COS-7 (e.g., ATCC CRL-1651); CHO, CHO-S Chinese hamster ovary cells; R1 mouse embryonic cells; E14.1 mouse embryonic cells; H1 human embryonic cells; H9 human embryonic cells; PER C.6, human embryonic cells; S. cerevisiae yeast cells; and picchia yeast cells. In one specific aspect, the eukaryotic cell production host cell line is CHO-S. In another specific aspect, the eukaryotic cell production host cell line is HEK293. In a further specific aspect, the eukaryotic cell production host cell line is CHOK1SV. In another specific aspect, the eukaryotic cell production host cell line is NS0.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

The method of the disclosure also comprises the step of expressing full length humanized antibodies in the cells to create a humanized antibody library. In one aspect, the cell is a eukaryotic cell production host with antibody cell surface display. In another aspect, one or both of the screening steps is performed in the eukaryotic cell production host.

Production of an Antibody

At least one humanized antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, antibodies, a Laboratory Manual, Cold Spring Harbor, N.Y. (1989). Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

In one approach, a hybridoma is produced by fusing a suitable immortal cell line (e.g., a myeloma cell line such as, but not limited to, Sp2/0, Sp2/0-AG14, NS0, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A), or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Antibodies of the present invention can also be prepared using at least one humanized antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616, 5,565,362; 5,304,489, and the like, each of which is entirely incorporated herein by reference.

Antibodies of the present invention can additionally be prepared using at least one humanized antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

Purification of an Antibody

A humanized antibody can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified antibodies can be characterized by, for example, ELISA, ELISPOT, flow cytometry, immunocytology, Biacore® analysis, Sapidyne KinExA™ kinetic exclusion assay, SDS-PAGE and Western blot, or by HPLC analysis as well as by a number of other functional assays disclosed herein.

The method of the disclosure also comprises the step of screening the humanized antibody library to determine the expression level of the humanized antibodies. The method of the disclosure also comprises the step of screening the humanized antibody library to determine the affinity of the humanized antibodies for the antigen compared to the affinity of the template antibody to the antigen. In one aspect, purified antibodies are screened. In another aspect, the eukaryotic cell production host is capable of antibody cell surface display, and the screening steps are performed in the eukaryotic cell production host.

In specific aspects, screening steps are selected from the group consisting of quantitative ELISA; affinity ELISA; ELISPOT; flow cytometry, immunocytology, Biacore® surface plasmon resonance analysis, Sapidyne KinExA™ kinetic exclusion assay; SDS-PAGE; Western blot, and HPLC analysis as well as by a number of other functional assays disclosed herein.

In other aspects of the present invention, downstream expression optimization in manufacturing hosts is performed by evolving the Fc region of the antibody, silent codons in the antibody, and/or the vector and/or host genes used in protein expression. In one aspect, an Fc library is generated by any evolutionary technique. In one specific aspect of expression optimization, CPE is performed on Fc domain of an antibody to create a library of Fc mutants which can be used to select an optimal partner for any Fv. Optimization is designed for rapid attachment of all Fc CPE variants to each new Fv region. Alternatively, a subset of these Fcs can be used to attach to different Fvs. Each of these Fc CPE variant/Fv combinations is screened as a full-length antibody expressed in mammalian cells (e.g. CHO, cost-effective media) for optimal expression. Further, CPS can be performed to screen all theoretical permutations of up to 12 or more of these CPE hits in mammalian cells for expression improvement. Specific desirable codon changes can also be selected to identify clones with increased expression. Silent codons are identified and CPE is performed on these positions. This CPE library is screened to identify optimal expression hits. Further, all theoretical permutations of up to 12 or more CPE hits can be used in the CPS process to generate a new library that can be screened in mammalian cells for expression improvement. The top CPS silent mutation hits are used to customize protein for optimal expression in a specific cell line and media. This provides opportunity for biosimilar fine structure control.

Other areas for enhancement of expression include: optimization of the vector, including promoter, splice sites, 5' and 3' termini, flanking sequences, reduction of gene deletion and rearrangement, improvement of host cell gene activities, optimization of host glycosylating enzymes, and chromosome wide host cell mutagenesis and selection. It has been demonstrated that 5' amino acid sequences are important for enhancement of expression.

EXAMPLES

Abbreviations:
BSA—bovine serum albumin
EIA—enzyme immunoassay
FBS—fetal bovine serum
$H_2O_2$—hydrogen peroxide
HRP—horseradish peroxidase
Ig—immunoglobulin
IL-6-Interleukin-6
IP—intraperitoneal
IV—intravenous
Mab—monoclonal antibody
OD—optical density
OPD—o-Phenylenediamine dihydrochloride
PEG—polyethylene glycol
PSA—penicillin, streptomycin, amphotericin
RT—room temperature
SQ—subcutaneous
v/v—volume per volume
w/v—weight per volume

Example 1

Example 1. Preparation of Heavy Chain and Light Chain Double Stranded DNA Fragments This protocol describes the preparation of double stranded (ds) DNA fragments which are used for the assembly of heavy chain and light chain variable domains [[SOP 2A)]]. The dsDNA fragments are prepared first by annealing synthetic oligonucleotides (oligos). The Oligos are 5'-phosphorylated to allow the fragments to ligate to each other and into the cloning vector.

Reagents, consumables and equipment required for this procedure are shown in Table 1.

TABLE 1

| Reagents, Consumables, and Equipment. | | |
|---|---|---|
| Description | Approved Supplier | Catalogue No. |
| SeaKem LE agarose | Cambrex | 50004 |
| Ethidium bromide | Sigma-Aldrich | E1510 |
| TAE buffer (10x) - 1000 ml | Ambion | 9869 |
| 1M Tris/HCl, pH 8.0 - 100 ml | Ambion | 9855G |
| 2M KCl - 100 ml | Ambion | 9640G |
| DTT (powder form) | Fisher | BP1725 |
| 1M MgCl2 - 100 ml | Ambion | 9530G |
| Nuclease free water - 5 × 100 ml | Ambion | 9939 |

TABLE 1-continued

Reagents, Consumables, and Equipment.

| Description | Approved Supplier | Catalogue No. |
|---|---|---|
| Agarose gel apparatus | Bio-Rad | 1707764 |
| Agarose gel power supply | Bio-Rad | 1645050 |
| 4% agarose gel | See Appendix 1 | N/A |
| Agarose gel loading buffer | Invitrogen | 10816-015 |
| 25 base pair (bp) DNA ladder | Invitrogen | 10597-011 |
| Microcentrifuge | Eppendorf | 5417C |
| High speed centrifuge | Beckman | Avanti J-30I |
| High speed centrifuge rotor | Beckman | |
| Thermo-mixer | Eppendorf | 5350-0000-013 |
| Thermo-cycler | MJ or Eppendorf | |
| PCR tubes | VWR | 53509-304 |
| 96 well PCR plate | VWR | |

Required Buffer Recipes are shown below.
50×TAE Buffer
    242 g Tris base
    57.1 ml glacial acetic acid
    37.2 g $Na_2EDTA$-$2H_2O$
    Add distilled $H_2O$ to final volume of 1 liter
1×TAE Buffer
    20 ml 50×TAE buffer
    800 ml distilled $H_2O$
0.1 M DTT
    1.54 g of DTT
    10 ml of distilled $H_2O$
    Store in −20° C.
80% Glycerol
    20 ml Glycerol
    80 ml distilled $H_2O$
    Sterilize by autoclaving
4% Agarose Gel with Ethidium Bromide
    4 g LE agarose
    100 ml 1×TAE buffer
    Melt the agarose in a microwave oven and swirl to ensure even mixing
    Cool agarose to 55° C.
    Add 2.5 µl of 20 mg/ml Ethidium Bromide to agarose
    Pour onto a gel platform
Procedures.

Oligonucleotides were ordered from IDT (1 µmol scale, PAGE purified, lyophilized and 5' phosphorylated). Lyophilized oligos were spun down in microcentrifuge at 12,000×g for 30 seconds before opening the tubes. Resuspend Oligos were resuspended in nuclease-free $H_2O$ at 100 pMole/µl according to the data obtained from IDT. Suspended oligos were incubated at 37° C. for 30 min in a thermomixer at 1,000 RPM. The re-suspended oligos were spun down in microcentrifuge at 12,000×g for 30 seconds and combined with 75 µl of matching forward and reverse primers in thin-wall PCR tubes (or 96 well PCR plates). The oligonucleotides were annealed in a thermocycler using the following temperature profile:

5' at 94° C.→5' at 90° C.→5' at 85° C.→5' at 80° C.→5' at 75° C.→5' at 70° C.→5' at 65° C.→5' at 60° C.→5' at 55° C.→5' at 50° C.→5' at 45° C.→5' at 40° C.→5' at 35° C.→5' at 30° C.

The final concentration for the annealed DNA fragment concentration was 50 pMole/µl. The annealed DNA fragments were stored at −20° C.

Quality control analysis of dsDNA fragments (or fragment pools), was performed by setting up the following reactions in 1.5 ml micro-centrifuge tubes:

| | |
|---|---|
| dsDNA fragments | 1 µl |
| Water | 20 µl |
| Sample loading buffer | 1 µl |
| Total | 22 µl |

Ten µl of each sample was loaded onto a 4% agarose TAE gel with 0.5 µg/ml Ethidium Bromide; a 25-bp DNA ladder was used as a standard. The gels were run at 100V for 20-30 minutes in 1×TAE buffer.

Standard references for the procedures include Current Protocols in Molecular biology. Edited by Ausubel, F., Brent, R., Kingston, R. E., Moore, D. D., Seidman, J. G., Smith, J. A., Struhl, K. John Wiley & Sons Inc.; Whitehouse, A., Deeble, J., Parmar, R., Taylor, G. R., Markham, A. F., and Meredith, D. M., Analysis of the mismatch and insertion/deletion binding properties of *Thermus thermophilus*, HB8, MutS. *Biochemical and Biophysical Research Communications* 233, 834-837; Wang, J. and L. J. Directly fishing out subtle mutations in genomic DNA with histidine-tagged *Thermus thermophilus* MutS. *Mutation Research* 547 (2004) 41-47.

Example 2. Liquid Phase Synthesis of Combinatorial Variable Domain Libraries-Heavy Chain This protocol describes the assembly of a humanized heavy chain (HC) variable domain library. The library contains human heavy chain frameworks (FW) and non-human complementarity determining regions (CDR) in the order of: FW1-CDR1-FW2-CDR2-FW3-CDR3. There are total of 7 FW1, 5 FW2 and 8 FW3 fragments. The library is assembled by using step wise liquid phase ligation of FW and CDR DNA fragments. A typical time of completion for this protocol is four days with creation of about four heavy chain libraries per person.

TABLE 2

Reagents, Consumables, and Equipment

| Item # | Description | Approved Supplier | Catalogue No. |
|---|---|---|---|
| 1 | 1M Tris/HCl, pH 8.0 - 100 ml | Ambion | 9855G |
| 2 | 0.5M EDTA, pH 8.0 - 100 ml | Ambion | 9260G |
| 3 | 5M NaCl - 500 ml | Ambion | 9759 |
| 4 | Tris base | Fisher | BP154-1 |
| 5 | Glacial acetic acid - 500 ml | Fisher | BP1185500 |
| 6 | $Na_2EDTA$-$2H_2O$ | Sigma-Aldrich | E9884 |
| 7 | Nuclease free water - 1000 ml | Ambion | 9932 |
| 8 | SeaKem LE agarose | Cambrex | 50004 |
| 9 | Ethidium bromide | Sigma-Aldrich | E1510 |
| 10 | Agarose gel power supply | Bio-Rad | 1645050 |
| 11 | Agarose gel appratus | Bio-Rad | 1707764 |
| 12 | 3% and 4% agarose gel | See Appendix 1 | N/A |
| 13 | Agarose gel loading buffer | Invitrogen | 10816-015 |
| 14 | 1 kB plus DNA ladder | Invitrogen | 10787-026 |
| 15 | Microcentrifuge | Eppendorf | 5417C |
| 16 | Thermomixer | Eppendorf | 5350-0000-013 |
| 17 | Labquake tube shakers | VWR | 56264-306 |
| 18 | Aluminum foil | In-house | N/A |
| 19 | 14 ml sterile Falcon polypropylene round bottom tube | VWR | 60819-761 |

TABLE 2-continued

Reagents, Consumables, and Equipment

| Item # | Description | Approved Supplier | Catalogue No. |
|---|---|---|---|
| 20 | 1.5 ml microcentrifuge tube | ISC Bioexpress | I5019-07 |
| 21 | PCR tubes strip with lids | VWR | 53509-304 |
| 22 | T4 DNA ligase (20,000 units) | NewEngland Biolab | M0202M |
| 23 | 10 mM rATP | Promega | P1132 |

Required Buffer Recipes are shown below.
50×TAE buffer
    242 g Tris base
    57.1 ml glacial acetic acid
    37.2 g $Na_2EDTA-2H_2O$
    Add distilled $H_2O$ to final volume of 1 liter
1×TAE Buffer
    20 ml 50×TAE buffer
    800 ml distilled $H_2O$
3% Agarose Gel with Ethidium Bromide
    3 g LE agarose
    100 ml 1×TAE buffer
    Melt the agarose in a microwave oven and swirl to ensure even mixing
    Cool agarose to 55° C.
    Add 2.5 µl of 20 mg/ml Ethidium Bromide to agarose
    Pour onto a gel platform
4% Agarose Gel with Ethidium Bromide
    4 g LE agarose
    100 ml 1×TAE buffer
    Melt the agarose in a microwave oven and swirl to ensure even mixing
    Cool agarose to 55° C.
    Add 2.5 µl of 20 mg/ml Ethidium Bromide to agarose
    Pour onto a gel platform The liquid phase synthesis procedures were followed as shown in stepwise format below. On Day 1, assembly of HC Variable Domain involves performing Ligation 1 and Ligation 2 at the same time, and performing Ligation 3 and Ligation 4 at the same time.

Ligation 1: FW1b→FW1a

Prepare the following ligation reactions in microcentrifuge tubes on ice. There are 7 ligation reactions (FW1-1 to FW1-7). Prepare each ligation reaction in a different microcentrifuge tube, total of 7 tubes.

| FW1a fragments (250 pMole) | x µL |
|---|---|
| FW1b fragments (250 pMole) | x µL |
| 10X T4 ligase Buffer | 2 µL |
| 10 mM rATP | 1 µL |
| Nuclease-free water | QS to 19 µL |
| T4 ligase | 1 µL |
| Total reaction volume | 20 µL |

1. Mix gently and spin briefly (5 sec.) in microfuge.
2. Incubate at room temperature for 1 hour.
3. Set up the following reactions in a 1.5 ml micro-centrifuge tube:

| FW1 ligations | 20 µl |
|---|---|
| 10x Sample loading buffer | 3 µl |
| Total Volume | 23 µl |

4. Load onto a 4% agarose TAE gel with 0.5 µg/ml Ethidium Bromide. Use 25 bp DNA ladder as standard. Run the gel at 100V for 20-30 minutes in 1×TAE buffer.
5. Cut out the bands corresponding to the correct sizes and purified using QIAquick Gel Extraction Kit.
6. Combine gel fragments from the 7 ligation reactions in two microcentrifuge tubes.
7. Add 3 volume of buffer QG to 1 volume of gel.
8. Incubate at 50° C. for 10 minutes until the gel slice has completely dissolved. Add 1 gel volume of isopropanol to the sample and mix.
9. Place a QIAquick spin column in a provided 2 ml collection tube.
10. Apply the sample to the QIAquick column, and centrifuge for 1 minute.
11. Discard flow-through and place QIAquick column back in the same collection tube.
12. Add 0.75 ml of buffer PE to QIAquick column and centrifuge for 1 minute.
13. Discard the flow-through and centrifuge the QIAquick column for an additional 1 minute at 17,900×g (13,000 rpm).
14. Place QIAquick column into a clean 1.5 ml microcentrifuge tube.
15. Add 52 µl of buffer EB to the center of the QIAquick membrane and centrifuge the column for 1 minute. Let the column stand for 1 minute, and then centrifuge for 1 minute.
16. Combine the eluted DNA (total volume of 104 µl) and load 6 µl on 4% agarose gel to QC the purified ligation products.

Ligation 2: FW3b→FW3a

17. Prepare the following ligation reactions in microcentrifuge tubes on ice. There are 8 ligation reactions (FW3-1 to FW3-8). Prepare each ligation reaction in a different microcentrifuge tube, total of 7 tubes.

| FW3a fragments (250 pMole) | x µL |
|---|---|
| FW3b fragments (250 pMole) | x µL |
| 10X T4 ligase Buffer | 2 µL |
| 10 mM rATP | 1 µL |
| Nuclease-free water | QS to 19 µL |
| T4 ligase | 1 µL |
| Total reaction volume | 20 µL |

18. Mix gently and spin briefly (5 sec.) in microfuge.
19. Incubate at room temperature for 1 hour.
20. Set up the following reactions in a 1.5 ml microcentrifuge tube:

| FW 3 ligations | 20 µL |
|---|---|
| 10x Sample loading buffer | 3 µL |
| Total Volume | 23 µL |

21. Load onto a 4% agarose TAE gel with 0.5 µg/ml Ethidium Bromide. Use 25 bp DNA ladder as standard. Run the gel at 100V for 20-30 minutes in 1×TAE buffer.
22. Cut out the bands corresponding to the correct sizes and purified using QIAquick Gel Extraction Kit.
23. Combine gel fragments from the 7 ligation reactions in two microcentrifuge tubes.

24. Add 3 volume of buffer QG to 1 volume of gel.
25. Incubate at 50° C. for 10 minutes until the gel slice has completely dissolved. Add 1 gel volume of isopropanol to the sample and mix.
26. Place a QIAquick spin column in a provided 2 ml collection tube.
27. Apply the sample to the QIAquick column, and centrifuge for 1 minute.
28. Discard flow-through and place QIAquick column back in the same collection tube.
29. Add 0.75 ml of buffer PE to QIAquick column and centrifuge for 1 minute.
30. Discard the flow-through and centrifuge the QIAquick column for an additional 1 minute at 17,900×g (13,000 rpm).
31. Place QIAquick column into a clean 1.5 ml microcentrifuge tube.
32. Add 52 µl of buffer EB to the center of the QIAquick membrane and centrifuge the column for 1 minute. Let the column stand for 1 minute, and then centrifuge for 1 minutes.
33. Combine the eluted DNA (total volume of 104 µl) and load 6 µl on 4% agarose gel to QC.

Ligation 3: CDR1→FW1

1. Prepare ligation reaction in a microcentrifuge tube on ice:

| | |
|---|---|
| CDR1 fragments (1 nMole) | x µL |
| Gel purified combined FW1 fragments | 94 µL |
| 10X T4 ligase Buffer | 14 µL |
| 10 mM rATP | 1 µL |
| Nuclease-free water | QS to 139 µL |
| T4 ligase | 1 µL |
| Total reaction volume | 140 µL |

2. Mix gently and spin briefly (5 sec.) in microfuge.
3. Incubate at room temperature for 1 hour.
4. Set up the following reactions in a 1.5 ml micro-centrifuge tube:

| | |
|---|---|
| CDR1-FW 1 ligations | 140 µl |
| 10x Sample loading buffer | 15 µl |
| Total Volume | 155 µl |

5. Load onto a 4% agarose TAE gel with 0.5 µg/ml Ethidium Bromide. Use 25 bp DNA ladder as standard. Run the gel at 100V for 20-30 minutes in 1×TAE buffer.
6. Cut out the bands corresponding to the correct sizes and purified using the QIAquick Gel Extraction Kit.
7. Combine the gel fragments in two microcentrifuge tubes.
8. Add 3 volume of buffer QG to 1 volume of gel.
9. Incubate at 50° C. for 10 minutes until the gel slice has completely dissolved. Add 1 gel volume of isopropanol to the sample and mix.
10. Place a QIAquick spin column in a provided 2 ml collection tube.
11. Apply the sample to the QIAquick column, and centrifuge for 1 minute.
12. Discard flow-through and place QIAquick column back in the same collection tube.
13. Add 0.75 ml of buffer PE to QIAquick column and centrifuge for 1 minute.
14. Discard the flow-through and centrifuge the QIAquick column for an additional 1 minute at 17,900×g (13,000 rpm).
15. Place QIAquick column into a clean 1.5 ml microcentrifuge tube.
16. Add 52 µl of buffer EB to the center of the QIAquick membrane and centrifuge the column for 1 minute. Let the column stand for 1 minute, and then centrifuge for 1 minute.
17. Combine the eluted DNA (total volume of 104 µl) and load 6 ul on 4% agarose gel to QC.

Ligation 4: CDR2→FW3

18. Prepare ligation reaction in a microcentrifuge tube on ice:

| | |
|---|---|
| CDR2 fragments (1 nMole) | x µL |
| Gel purified combined FW3 fragments | 94 µL |
| 10X T4 ligase Buffer | 14 µL |
| 10 mM rATP | 1 µL |
| Nuclease-free water | QS to 139 µL |
| T4 ligase | 1 µL |
| Total reaction volume | 140 µL |

19. Mix gently and spin briefly (5 sec.) in microfuge.
20. Incubate at room temperature for 1 hour.
21. Set up the following reactions in a 1.5 ml micro-centrifuge tube:

| | |
|---|---|
| CDR2-FW3 ligations | 140 µl |
| 10x Sample loading buffer | 15 µl |
| Total Volume | 155 µl |

22. Load onto a 4% agarose TAE gel with 0.5 µg/ml Ethidium Bromide. Use 25 bp DNA ladder as standard. Run the gel at 100V for 20-30 minutes in 1×TAE buffer.
23. Cut out the bands corresponding to the correct sizes and purified using the QIAquick Gel Extraction Kit.
24. Combine the gel fragments in two microcentrifuge tubes.
25. Add 3 volume of buffer QG to 1 volume of gel.
26. Incubate at 50° C. for 10 minutes until the gel slice has completely dissolved. Add 1 gel volume of isopropanol to the sample and mix.
27. Place a QIAquick spin column in a provided 2 ml collection tube.
28. Apply the sample to the QIAquick column, and centrifuge for 1 minute.
29. Discard flow-through and place QIAquick column back in the same collection tube.
30. Add 0.75 ml of buffer PE to QIAquick column and centrifuge for 1 minute.
31. Discard the flow-through and centrifuge the QIAquick column for an additional 1 minute at 17,900×g (13,000 rpm).
32. Place QIAquick column into a clean 1.5 ml microcentrifuge tube.
33. Add 52 µl of buffer EB to the center of the QIAquick membrane and centrifuge the column for 1 minute. Let the column stand for 1 minute, and then centrifuge for 1 minute.
34. Combine the eluted DNA (total volume of 104 µl) and load 6 µl on 4% agarose gel to QC.

On Day 2, assembly of HC variable domain was continued by performing Ligation 5 and Ligation 6 at the same time Ligation 5: FW2→CDR1-FW1

1. Prepare ligation reaction in a microcentrifuge tube on ice:

| | |
|---|---:|
| FW2 fragment pool (450 pMole) | x μL |
| Gel purified CDR1-FW1 fragments | 94 μL |
| 10X T4 ligase Buffer | 14 μL |
| 10 mM rATP | 1 μL |
| Nuclease-free water | QS to 139 μL |
| T4 ligase | 1 μL |
| Total reaction volume | 140 μL |

The FW2 fragment pool contained 5 FW2 fragments, each at 90 pMole.

2. Mix gently and spin briefly (5 sec.) in microfuge.
3. Incubate at room temperature for 1 hour.
4. Set up the following reactions in a 1.5 ml micro-centrifuge tube:

| | |
|---|---:|
| FW2-CDR-1-FW1 ligations | 140 μl |
| 10x Sample loading buffer | 15 μl |
| Total Volume | 155 μl |

5. Load onto a 4% agarose TAE gel with 0.5 μg/ml Ethidium Bromide. Use 25 bp DNA ladder as standard. Run the gel at 100V for 20-30 minutes in 1×TAE buffer.
6. Cut out the bands corresponding to the correct sizes and purified using QIAquick Gel Extraction Kit.
7. Combine gel fragments from the 7 ligation reactions in two microcentrifuge tubes.
8. Add 3 volume of buffer QG to 1 volume of gel.
9. Incubate at 50° C. for 10 minutes until the gel slice has completely dissolved. Add 1 gel volume of isopropanol to the sample and mix.
10. Place a QIAquick spin column in a provided 2 ml collection tube.
11. Apply the sample to the QIAquick column, and centrifuge for 1 minute.
12. Discard flow-through and place QIAquick column back in the same collection tube.
13. Add 0.75 ml of buffer PE to QIAquick column and centrifuge for 1 minute.
14. Discard the flow-through and centrifuge the QIAquick column for an additional 1 minute at 17,900×g (13,000 rpm).
15. Place QIAquick column into a clean 1.5 ml microcentrifuge tube.
16. Add 30 μL of buffer EB to the center of the QIAquick membrane and centrifuge the column for 1 minute. Let the column stand for 1 minute, and then centrifuge for 1 minutes.
17. Combine the eluted DNA (total volume of 60 μL) and load 3 μL on 4% agarose gel to QC.

Ligation 6: CDR3→FW3-CDR2

18. Prepare ligation reaction in a microcentrifuge tube on ice:

| | |
|---|---:|
| CDR3 fragment pool (500 pMole) | x μL |
| Gel purified FW3-CDR2 fragments | 94 μL |
| 10X T4 ligase Buffer | 14 μL |
| 10 mM rATP | 1 μL |
| Nuclease-free water | QS to 139 μL |
| T4 ligase | 1 μL |
| Total reaction volume | 140 μL |

[[The FW2 fragment pool contained 5 FW2 fragments, each at 90 pMole]]

19. Mix gently and spin briefly (5 sec.) in microfuge.
20. Incubate at room temperature for 1 hour.
21. Set up the following reactions in a 1.5 ml micro-centrifuge tube:

| | |
|---|---:|
| CDR3-FW3-CDR2 ligations | 140 μl |
| 10x Sample loading buffer | 15 μl |
| Total Volume | 155 μl |

22. Load onto a 4% agarose TAE gel with 0.5 μg/ml Ethidium Bromide. Use 25 bp DNA ladder as standard. Run the gel at 100V for 20-30 minutes in 1×TAE buffer.
23. Cut out the bands corresponding to the correct sizes and purified using QIAquick Gel Extraction Kit.
24. Combine gel fragments from the 7 ligation reactions in two microcentrifuge tubes.
25. Add 3 volume of buffer QG to 1 volume of gel.
26. Incubate at 50° C. for 10 minutes until the gel slice has completely dissolved. Add 1 gel volume of isopropanol to the sample and mix.
27. Place a QIAquick spin column in a provided 2 ml collection tube.
28. Apply the sample to the QIAquick column, and centrifuge for 1 minute.
29. Discard flow-through and place QIAquick column back in the same collection tube.
30. Add 0.75 ml of buffer PE to QIAquick column and centrifuge for 1 minute.
31. Discard the flow-through and centrifuge the QIAquick column for an additional 1 minute at 17,900×g (13,000 rpm).
32. Place QIAquick column into a clean 1.5 ml microcentrifuge tube.
33. Add 30 μL of buffer EB to the center of the QIAquick membrane and centrifuge the column for 1 minute. Let the column stand for 1 minute, and then centrifuge for 1 minute.

34. Combine the eluted DNA (total volume of 60 μL) and load 3 μL on 4% agarose gel to QC.

Ligation 7: Full Length HC Variable Domain
1. Prepare ligation reactions in a microcentrifuge tube on ice:

| | |
|---|---|
| FW1-CDR1-FW2 fragments | 49 μL |
| CDR2-FW3-CDR3 fragments | 49 μL |
| 10X T4 ligase Buffer | 12 μL |
| 10 mM rATP | 5 μL |
| Nuclease-free water | QS to 345 μL |
| T4 ligase | 5 μL |
| Total reaction volume | 350 μL |

35. Mix gently and spin briefly (5 sec.) in microfuge.
36. Incubate at room temperature for 1 hour.
37. Set up the following reactions in a 1.5 ml microcentrifuge tube:

| | |
|---|---|
| Full length HC variable domain ligations | 140 μl |
| 10x Sample loading buffer | 15 μl |
| Total Volume | 155 μl |

38. Load onto a 3% agarose TAE gel with 0.5 μg/ml Ethidium Bromide. Use 100 bp DNA ladder as standard. Run the gel at 100V for 20-30 minutes in 1×TAE buffer.
39. Cut out the bands corresponding to the correct sizes and purified using QIAquick Gel Extraction Kit.
40. Combine gel fragments in one microcentrifuge tube.
41. Add 3 volume of buffer QG to 1 volume of gel.
42. Incubate at 50° C. for 10 minutes until the gel slice has completely dissolved. Add 1 gel volume of isopropanol to the sample and mix.
43. Place a QIAquick spin column in a provided 2 ml collection tube.
44. Apply the sample to the QIAquick column, and centrifuge for 1 minute.
45. Discard flow-through and place QIAquick column back in the same collection tube.
46. Add 0.75 ml of buffer PE to QIAquick column and centrifuge for 1 minute.
47. Discard the flow-through and centrifuge the QIAquick column for an additional 1 minute at 17,900×g (13,000 rpm).
48. Place QIAquick column into a clean 1.5 ml microcentrifuge tube.
49. Add 30 μl of buffer EB to the center of the QIAquick membrane and centrifuge the column for 1 minute. Let the column stand for 1 minute, and then centrifuge for 1 minute.
50. Load 3 μl on 3% agarose gel to QC.

Determining the Heavy Chain CDRs. The following set of rules allows the identification of the CDRs in most antibody heavy chain variable domain sequences.
CDR-H1
Start: ~position 26, always 4 after a cysteine residue
Residues before: C-X-X-X
Length: 10-12 amino acids
Residues after: always a W, usually W-V, but also W-I, W-A
CDR-H2
Start: always 15 residues after the end of CDR-H1
Residues before: usually L-E-W-I-G, but a number of variations
Length: 16-19 amino acids
Residues after: K/R-L/I/V/F/T/A-T/S/I/A
CDR-H3
Start: always 33 residues after end of CDR-H2 (always 2 after a cysteine)
Residues before: always C-X-X, usually C-A-R
Length: 3-25 residues
Residues after: W-G-X-G (typically W-G-Q-G)

References for this protocol include L. B. K. C. Antibody humanization by CDR grafting. Antibody Engineering, Methods and protocols. Edit by Benny K. C. Lo, Methods in Molecular Biology, 2004; 248, 135-159; Developing a minimally immunogenic humanized antibody by SDR grafting. Antibody Engineering, Methods and protocols. Edit by Benny K. C. Lo, Methods in Molecular Biology, 2004, 248, 361-376; Bassette, P. H., Mena, M. A., Nguyen, A. W. and Daugherty, P. S. Construction of Designed Protein Libraries Using Gene Assembly Mutagenesis. Directed Evolution Library Creation, Methods and protocols. Edit by Frances H. Arnold and George Georgiou, Methods in Molecular Biology, 2003, 231, 29-37; Chames, P., Hoogenboom, H. R., and Henderikx, P. Selection on Biotinylated antigens. Antibody Engineering, Edit by R. Kontermann and S. Dubel, Springer Lab Manual, 149-166; Obrien S., and Jones, T. Humanising antibodies by CDR grafting. Antibody Engineering, Edit by R. Kontermann and S. Dubel, Springer Lab Manual, 567-590.

Example 3. Liquid Phase Synthesis of Combinatorial Variable Domain Libraries—Light Chain This protocol describes the assembly of a humanized light chain (LC) variable domain library. The library contains human light chain frameworks (FW) and non-human complementarity determining regions (CDR) in the order of: FW1-CDR1-FW2-CDR2-FW3-CDR3. There are total of 7 FW1, 4 FW2 and 8 FW3 fragments. The library is assembled by using step wise liquid phase ligation of FW and CDR DNA fragments. A typical time of completion for this protocol is four days with creation of about four heavy chain libraries per person. Reagents, consumables and equipment is described in Example 2, Table 2, above. Required Buffer Recipes are shown above in Example 2.

The liquid phase synthesis procedures were followed as shown in stepwise format below. On Day 1, assembly of HC Variable Domain involves performing Ligation 1 and Ligation 2 at the same time, and performing Ligation 3 and Ligation 4 at the same time.

Ligation 1: FW1b→FW1a
34. Prepare the following ligation reactions in microcentrifuge tubes on ice. There are 7 ligation reactions (FW1-1 to FW1-7). Prepare each ligation reaction in a different microcentrifuge tube, total of 7 tubes.

| | |
|---|---|
| FW1a fragments (250 pMole) | x μL |
| FW1b fragments (250 pMole) | x μL |
| 10X T4 ligase Buffer | 2 μL |
| 10 mM rATP | 1 μL |
| Nuclease-free water | QS to 19 μL |
| T4 ligase | 1 μL |
| Total reaction volume | 20 μL |

35. Mix gently and spin briefly (5 sec.) in microfuge.
36. Incubate at room temperature for 1 hour.

37. Set up the following reactions in a 1.5 ml microcentrifuge tube:

| | |
|---|---|
| FW1 ligations | 20 µl |
| 10x Sample loading buffer | 3 µl |
| Total Volume | 23 µl |

38. Load onto a 4% agarose TAE gel with 0.5 µg/ml Ethidium Bromide. Use 25 bp DNA ladder as standard. Run the gel at 100V for 20-30 minutes in 1×TAE buffer.
39. Cut out the bands corresponding to the correct sizes and purified using QIAquick Gel Extraction Kit.
40. Combine gel fragments from the 7 ligation reactions in two microcentrifuge tubes.
41. Add 3 volume of buffer QG to 1 volume of gel.
42. Incubate at 50° C. for 10 minutes until the gel slice has completely dissolved. Add 1 gel volume of isopropanol to the sample and mix.
43. Place a QIAquick spin column in a provided 2 ml collection tube.
44. Apply the sample to the QIAquick column, and centrifuge for 1 minute.
45. Discard flow-through and place QIAquick column back in the same collection tube.
46. Add 0.75 ml of buffer PE to QIAquick column and centrifuge for 1 minute.
47. Discard the flow-through and centrifuge the QIAquick column for an additional 1 minute at 17,900×g (13,000 rpm).
48. Place QIAquick column into a clean 1.5 ml microcentrifuge tube.
49. Add 52 µl of buffer EB to the center of the QIAquick membrane and centrifuge the column for 1 minute. Let the column stand for 1 minute, and then centrifuge for 1 minute.
50. Combine the eluted DNA (total volume of 104 µl) and load 6 µl on 4% agarose gel to QC the purified ligation products.

Ligation 2: FW3b→FW3a

51. Prepare the following ligation reactions in microcentrifuge tubes on ice. There are 8 ligation reactions (FW3-1 to FW3-8). Prepare each ligation reaction in a different microcentrifuge tube, total of 7 tubes.

| | |
|---|---|
| FW3a fragments (250 pMole) | x µL |
| FW3b fragments (250 pMole) | x µL |
| 10X T4 ligase Buffer | 2 µL |
| 10 mM rATP | 1 µL |
| Nuclease-free water | QS to 19 µL |
| T4 ligase | 1 µL |
| Total reaction volume | 20 µL |

52. Mix gently and spin briefly (5 sec.) in microfuge.
53. Incubate at room temperature for 1 hour.
54. Set up the following reactions in a 1.5 ml microcentrifuge tube:

| | |
|---|---|
| FW 3 ligations | 20 µL |
| 10x Sample loading buffer | 3 µL |
| Total Volume | 23 µL |

55. Load onto a 4% agarose TAE gel with 0.5 µg/ml Ethidium Bromide. Use 25 bp DNA ladder as standard. Run the gel at 100V for 20-30 minutes in 1×TAE buffer.
56. Cut out the bands corresponding to the correct sizes and purified using QIAquick Gel Extraction Kit.
57. Combine gel fragments from the 7 ligation reactions in two microcentrifuge tubes.
58. Add 3 volume of buffer QG to 1 volume of gel.
59. Incubate at 50° C. for 10 minutes until the gel slice has completely dissolved. Add 1 gel volume of isopropanol to the sample and mix.
60. Place a QIAquick spin column in a provided 2 ml collection tube.
61. Apply the sample to the QIAquick column, and centrifuge for 1 minute.
62. Discard flow-through and place QIAquick column back in the same collection tube.
63. Add 0.75 ml of buffer PE to QIAquick column and centrifuge for 1 minute.
64. Discard the flow-through and centrifuge the QIAquick column for an additional 1 minute at 17,900×g (13,000 rpm).
65. Place QIAquick column into a clean 1.5 ml microcentrifuge tube.
66. Add 52 µL of buffer EB to the center of the QIAquick membrane and centrifuge the column for 1 minute. Let the column stand for 1 minute, and then centrifuge for 1 minutes.
67. Combine the eluted DNA (total volume of 104 µL) and load 6 µL on 4% agarose gel to QC.

Ligation 3: CDR1→FW1

35. Prepare ligation reaction in a microcentrifuge tube on ice:

| | |
|---|---|
| CDR1 fragments (1 nMole) | x µL |
| Gel purified combined FW1 fragments | 94 µL |
| 10X T4 ligase Buffer | 14 µL |
| 10 mM rATP | 1 µL |
| Nuclease-free water | QS to 139 µL |
| T4 ligase | 1 µL |
| Total reaction volume | 140 µL |

36. Mix gently and spin briefly (5 sec.) in microfuge.
37. Incubate at room temperature for 1 hour.
38. Set up the following reactions in a 1.5 ml microcentrifuge tube:

| | |
|---|---|
| CDR1-FW 1 ligations | 140 µl |
| 10x Sample loading buffer | 15 µl |
| Total Volume | 155 µl |

39. Load onto a 4% agarose TAE gel with 0.5 µg/ml Ethidium Bromide. Use 25 bp DNA ladder as standard. Run the gel at 100V for 20-30 minutes in 1×TAE buffer.
40. Cut out the bands corresponding to the correct sizes and purified using the QIAquick Gel Extraction Kit.
41. Combine the gel fragments in two microcentrifuge tubes.
42. Add 3 volume of buffer QG to 1 volume of gel.
43. Incubate at 50° C. for 10 minutes until the gel slice has completely dissolved. Add 1 gel volume of isopropanol to the sample and mix.
44. Place a QIAquick spin column in a provided 2 ml collection tube.

45. Apply the sample to the QIAquick column, and centrifuge for 1 minute.
46. Discard flow-through and place QIAquick column back in the same collection tube.
47. Add 0.75 ml of buffer PE to QIAquick column and centrifuge for 1 minute.
48. Discard the flow-through and centrifuge the QIAquick column for an additional 1 minute at 17,900×g (13,000 rpm).
49. Place QIAquick column into a clean 1.5 ml microcentrifuge tube.
50. Add 52 µl of buffer EB to the center of the QIAquick membrane and centrifuge the column for 1 minute. Let the column stand for 1 minute, and then centrifuge for 1 minute.
51. Combine the eluted DNA (total volume of 104 µl) and load 6 ul on 4% agarose gel to QC.

Ligation 4: CDR2→FW3

52. Prepare ligation reaction in a microcentrifuge tube on ice:

| | |
|---|---|
| CDR2 fragments (1 nMole) | x µL |
| Gel purified combined FW3 fragments | 94 µL |
| 10X T4 ligase Buffer | 14 µL |
| 10 mM rATP | 1 µL |
| Nuclease-free water | QS to 139 µL |
| T4 ligase | 1 µL |
| Total reaction volume | 140 µL |

53. Mix gently and spin briefly (5 sec.) in microfuge.
54. Incubate at room temperature for 1 hour.
55. Set up the following reactions in a 1.5 ml microcentrifuge tube:

| | |
|---|---|
| CDR2-FW3 ligations | 140 µl |
| 10x Sample loading buffer | 15 µl |
| Total Volume | 155 µl |

56. Load onto a 4% agarose TAE gel with 0.5 µg/ml Ethidium Bromide. Use 25 bp DNA ladder as standard. Run the gel at 100V for 20-30 minutes in 1×TAE buffer.
57. Cut out the bands corresponding to the correct sizes and purified using the QIAquick Gel Extraction Kit.
58. Combine the gel fragments in two microcentrifuge tubes.
59. Add 3 volume of buffer QG to 1 volume of gel.
60. Incubate at 50° C. for 10 minutes until the gel slice has completely dissolved. Add 1 gel volume of isopropanol to the sample and mix.
61. Place a QIAquick spin column in a provided 2 ml collection tube.
62. Apply the sample to the QIAquick column, and centrifuge for 1 minute.
63. Discard flow-through and place QIAquick column back in the same collection tube.
64. Add 0.75 ml of buffer PE to QIAquick column and centrifuge for 1 minute.
65. Discard the flow-through and centrifuge the QIAquick column for an additional 1 minute at 17,900×g (13,000 rpm).
66. Place QIAquick column into a clean 1.5 ml microcentrifuge tube.
67. Add 52 µL of buffer EB to the center of the QIAquick membrane and centrifuge the column for 1 minute. Let the column stand for 1 minute, and then centrifuge for 1 minute.
68. Combine the eluted DNA (total volume of 104 µL) and load 6 µL on 4% agarose gel to QC.

On Day 2, assembly of HC variable domain was continued by performing Ligation 5 and Ligation 6 at the same time Ligation 5: FW2→CDR1-FW1

51. Prepare ligation reaction in a microcentrifuge tube on ice:

| | |
|---|---|
| FW2 fragment pool (450 pMole) | x µL |
| Gel purified CDR1-FW1 fragments | 94 µL |
| 10X T4 ligase Buffer | 14 µL |
| 10 mM rATP | 1 µL |
| Nuclease-free water | QS to 139 µL |
| T4 ligase | 1 µL |
| Total reaction volume | 140 µL |

The FW2 fragment pool contained 5 FW2 fragments, each at 90 pMole.

52. Mix gently and spin briefly (5 sec.) in microfuge.
53. Incubate at room temperature for 1 hour.
54. Set up the following reactions in a 1.5 ml microcentrifuge tube:

| | |
|---|---|
| FW2-CDR-1-FW1 ligations | 140 µl |
| 10x Sample loading buffer | 15 µl |
| Total Volume | 155 µl |

55. Load onto a 4% agarose TAE gel with 0.5 µg/ml Ethidium Bromide. Use 25 bp DNA ladder as standard. Run the gel at 100V for 20-30 minutes in 1×TAE buffer.
56. Cut out the bands corresponding to the correct sizes and purified using QIAquick Gel Extraction Kit.
57. Combine gel fragments from the 7 ligation reactions in two microcentrifuge tubes.
58. Add 3 volume of buffer QG to 1 volume of gel.
59. Incubate at 50° C. for 10 minutes until the gel slice has completely dissolved. Add 1 gel volume of isopropanol to the sample and mix.
60. Place a QIAquick spin column in a provided 2 ml collection tube.
61. Apply the sample to the QIAquick column, and centrifuge for 1 minute.
62. Discard flow-through and place QIAquick column back in the same collection tube.
63. Add 0.75 ml of buffer PE to QIAquick column and centrifuge for 1 minute.
64. Discard the flow-through and centrifuge the QIAquick column for an additional 1 minute at 17,900×g (13,000 rpm).
65. Place QIAquick column into a clean 1.5 ml microcentrifuge tube.
66. Add 30 µL of buffer EB to the center of the QIAquick membrane and centrifuge the column for 1 minute. Let the column stand for 1 minute, and then centrifuge for 1 minutes.
67. Combine the eluted DNA (total volume of 60 µL) and load 3 µL on 4% agarose gel to QC.

Ligation 6: CDR3→FW3-CDR2

68. Prepare ligation reaction in a microcentrifuge tube on ice:

| CDR3 fragment pool (500 pMole) | x µL |
|---|---|
| Gel purified FW3-CDR2 fragments | 94 µL |
| 10X T4 ligase Buffer | 14 µL |
| 10 mM rATP | 1 µL |
| Nuclease-free water | QS to 139 µL |
| T4 ligase | 1 µL |
| Total reaction volume | 140 µL |

[[The FW2 fragment pool contained 4 FW2 fragments, each at 90 pMole]]

69. Mix gently and spin briefly (5 sec.) in microfuge.
70. Incubate at room temperature for 1 hour.
71. Set up the following reactions in a 1.5 ml microcentrifuge tube:

| CDR3-FW3-CDR2 ligations | 140 µl |
|---|---|
| 10x Sample loading buffer | 15 µl |
| Total Volume | 155 µl |

72. Load onto a 4% agarose TAE gel with 0.5 µg/ml Ethidium Bromide. Use 25 bp DNA ladder as standard. Run the gel at 100V for 20-30 minutes in 1×TAE buffer.
73. Cut out the bands corresponding to the correct sizes and purified using QIAquick Gel Extraction Kit.
74. Combine gel fragments from the 7 ligation reactions in two microcentrifuge tubes.
75. Add 3 volume of buffer QG to 1 volume of gel.
76. Incubate at 50° C. for 10 minutes until the gel slice has completely dissolved. Add 1 gel volume of isopropanol to the sample and mix.
77. Place a QIAquick spin column in a provided 2 ml collection tube.
78. Apply the sample to the QIAquick column, and centrifuge for 1 minute.
79. Discard flow-through and place QIAquick column back in the same collection tube.
80. Add 0.75 ml of buffer PE to QIAquick column and centrifuge for 1 minute.
81. Discard the flow-through and centrifuge the QIAquick column for an additional 1 minute at 17,900×g (13,000 rpm).
82. Place QIAquick column into a clean 1.5 ml microcentrifuge tube.
83. Add 30 µL of buffer EB to the center of the QIAquick membrane and centrifuge the column for 1 minute. Let the column stand for 1 minute, and then centrifuge for 1 minute.
84. Combine the eluted DNA (total volume of 60 µL) and load 3 µL on 4% agarose gel to QC.

Ligation 7: Full Length LC Variable Domain

2. Prepare ligation reactions in a microcentrifuge tube on ice:

| FW1-CDR1-FW2 fragments | 49 µL |
|---|---|
| CDR2-FW3-CDR3 fragments | 49 µL |
| 10X T4 ligase Buffer | 12 µL |
| 10 mM rATP | 5 µL |
| Nuclease-free water | QS to 345 µL |
| T4 ligase | 5 µL |
| Total reaction volume | 350 µL |

85. Mix gently and spin briefly (5 sec.) in microfuge.
86. Incubate at room temperature for 1 hour.
87. Set up the following reactions in a 1.5 ml microcentrifuge tube:

| Full length LC variable domain ligations | 140 µl |
|---|---|
| 10x Sample loading buffer | 15 µl |
| Total Volume | 155 µl |

88. Load onto a 3% agarose TAE gel with 0.5 µg/ml Ethidium Bromide. Use 100 bp DNA ladder as standard. Run the gel at 100V for 20-30 minutes in 1×TAE buffer.
89. Cut out the bands corresponding to the correct sizes and purified using QIAquick Gel Extraction Kit.
90. Combine gel fragments in one microcentrifuge tube.
91. Add 3 volume of buffer QG to 1 volume of gel.
92. Incubate at 50° C. for 10 minutes until the gel slice has completely dissolved. Add 1 gel volume of isopropanol to the sample and mix.
93. Place a QIAquick spin column in a provided 2 ml collection tube.
94. Apply the sample to the QIAquick column, and centrifuge for 1 minute.
95. Discard flow-through and place QIAquick column back in the same collection tube.
96. Add 0.75 ml of buffer PE to QIAquick column and centrifuge for 1 minute.
97. Discard the flow-through and centrifuge the QIAquick column for an additional 1 minute at 17,900×g (13,000 rpm).
98. Place QIAquick column into a clean 1.5 ml microcentrifuge tube.
99. Add 30 µl of buffer EB to the center of the QIAquick membrane and centrifuge the column for 1 minute. Let the column stand for 1 minute, and then centrifuge for 1 minute.
100. Load 3 µl on 3% agarose gel to QC.

Determining the light chain CDRs. The following set of rules allows the identification of the CDRs in most antibody light chain variable domain sequences.

CDR-L1
Start: ~position 24, always 1 after a cysteine residue
Residues before: C
Length: 10-17 amino acids
Residues after: always a W, usually W-Y-Q, but also W-L-Q, W-F-Q, W-Y-L CDR-L2
Start: always 16 residues after the end of CDR-L1
Residues before: usually I-Y, but also V-Y, I-K, I-F
Length: always 7 amino acids CDR-L3
Start: always 33 residues after end of CDR-L2 (always 2 after a cysteine)
Residues before: always C
Length: 7-11 residues
Residues after: F-G-X-G (typically F-G-Q-G)

Example 4. Cloning of Assembled Variable Domains. Ligation of HC and LC Variable Domain with Fc This protocol describes the cloning of assembled humanized heavy and light chain variable domains into BioAtla expression vectors, pBA-K and pBA-L. The estimated time of completion 7 days with 4 cloning procedures per person. Table 3 shows required reagents, consumables and equipment.

TABLE 3

Reagents, Consumables, and Equipment

| Item # | Description | Approved Supplier | Catalogue No. |
|---|---|---|---|
| 1 | 1 kB plus DNA ladder | Invitrogen | 10787-026 |
| 2 | 1% agarose gel | See Appendix 1 | N/A |
| 3 | 1.5 ml microcentrifuge tube | ISC Bioexpress | I5019-07 |
| 4 | 14 ml sterile Falcon polypropylene round bottom tube | VWR | 60819-761 |
| 5 | 5M NaCl - 500 ml | Ambion | 9759 |
| 6 | Agar | | |
| 7 | Agarose gel appratus | Bio-Rad | 1707764 |
| 8 | Agarose gel loading buffer | Invitrogen | 10816-015 |
| 9 | Agarose gel power supply | Bio-Rad | 1645050 |
| 10 | BsaI | New England Biolab | R0535S |
| 11 | BsmBI | New England Biolab | R0580L |
| 12 | Ethidium bromide | Sigma-Aldrich | E1510 |
| 13 | Glacial acetic acid - 500 ml | Fisher | BP1185500 |
| 14 | Microcentrifuge | Eppendorf | 5417C |
| 15 | $Na_2EDTA\text{-}2H_2O$ | Sigma-Aldrich | E9884 |
| 16 | Nuclease free water - 1000 ml | Ambion | 9932 |
| 17 | PCR tubes strip with lids | VWR | 53509-304 |
| 18 | Plate scraper | | |
| 19 | Plating beads | | |
| 20 | QIAprep Sping miniprep kit | Qiagen | 27104 |
| 21 | QIAquick PCR purification kit | Qiagen | 28104 |
| 22 | SeaKem LE agarose | Cambrex | 50004 |
| 23 | T4 DNA ligase (20,000 units) | NewEngland Biolab | M0202T |
| 24 | Tris base | Fisher | BP154-1 |
| 25 | Tryptone | | |
| 26 | Water bath | | |
| 27 | XLI Blue Supercompetent cells | Stratagene | 200236 |
| 28 | Yeast Extract | | |

The following buffers are required for this protocol.
50×TAE Buffer
    242 g Tris base
    57.1 ml glacial acetic acid
    37.2 g $Na_2EDTA\text{-}2H_2O$
    Add distilled $H_2O$ to final volume of 1 liter
1×TAE Buffer
    20 ml 50×TAE buffer
    800 ml distilled $H_2O$
1% Agarose Gel with Ethidium Bromide
    1 g LE agarose
    100 ml 1×TAE buffer
    Melt the agarose in a microwave oven and swirl to ensure even mixing
    Cool agarose to 55° C.
    Add 2.5 μl of 20 mg/ml Ethidium Bromide to agarose
    Pour onto a gel platform
LB
    10 g NaCl
    10 g tryptone
    5 g yeast extract
    Add distilled $H_2O$ to a final volume of 1 liter
    Adjust pH to 7.0 with 5 N NaOH
    Autoclave
LB-Carbenicillin Agar
    10 g NaCl
    10 g tryptone
    5 g yeast extract
    20 g agar
    Add distilled $H_2O$ to a final volume of 1 liter
    Adjust pH to 7.0 with 5 N NaOH
    Autoclave
    Cool to 55° C.
    Add 10 ml of 10 mg/ml of filter-sterilized carbenicillin
    Pour into petri dishes (25 ml/100-mm plate)
SOC Medium
    0.5 g NaCl
    20 g tryptone
    0.5 g yeast extract
    2 ml of filter-sterilized 20% glucose
    Add distilled $H_2O$ to a final volume of 1 liter
    Autoclave
    Add 10 ml of filter-sterilized 1 M $MgCl_2$ and 10 ml of filter-sterilized 1 M $MgSO_s$ prior to use On Day 1 digest pBA vector with BsaI. Prepare the following digestion reaction in a microcentrifuge tube on ice:

| pBA (5 ug) | x μL |
|---|---|
| 10X NEB Buffer 3 | 10 μL |
| Nuclease-free water | QS to 97 μL |
| BsaI (10 U/μL) | 3 μL |
| Total reaction volume | 100 μL |

1. Mix gently and spin briefly (5 sec.) in microfuge
2. Incubate the reaction at 50° C. overnight
Day 2
3. Add 2 μL of Apex phosphatase to the microcentrifuge tube
4. Incubate at 37° C. for 10 minutes
5. Heat at 70° C. for 5 minutes to inactivate the Apex phosphatase
Purify BsaI digested pBA vector with QIAquick PCR Purification Kit
6. Add 500 μL of Buffer PBI to the microcentrifuge
7. Mix by vortexing and quick centrifuge
8. Load 750 μL at a time onto a column
9. Centrifuge at 12,000×g for 1 minute and decant liquid from collection tube
10. Repeat until all sample has been processed.
11. Wash with 750 μL PE Buffer (Ethanol added!)
12. Centrifuge at 12, 000×g for 1 minute and decant liquid from collection tube
13. Place column back onto collection tube and centrifuge again
14. Put column onto new microcentrifuge tubes and elute with 50 μL EB Buffer
Quality Control Analysis
1. To QC the BsaI digested pBA vector, set up the following reactions in a 1.5 ml micro-centrifuge tube:

| pBA-BsaI | 2 μl | pBA-uncut | 2 μl |
|---|---|---|---|
| Water | 7 μl | Water | 7 μl |
| Sample loading buffer | 1 μl | Sample loading buffer | 1 μl |
| Total Volume | 10 μl | Total Volume | 10 μl |

2. Load 10 μL onto a 1% agarose TAE gel with 0.5 μg/ml Ethidium Bromide. Use 1 kb plus DNA ladder as standard. Run the gel at 100V for 20-30 minutes in 1×TAE buffer.

3. Determine the concentration of the BsaI digested pBA vector with spectrophotometer ($OD_{260/280}$)
4. Set up the following ligation reactions to determine the background and ligation efficiency of the BsaI digested pBA vector:

| a. Vector Background Ligation | |
|---|---|
| pBA-BsaI (100 ng) | x μL |
| 5X T4 ligase Buffer | 4 μL |
| Nuclease-free water | QS to 19 μL |
| T4 ligase (2,000 U/μL) | 1 μL |
| Total reaction volume | 20 μL |

| b. Test Insert Ligations | |
|---|---|
| pBA-BsaI (100 ng) | x μL |
| Test insert (5 ng, 10 ng) | y μL |
| 5X T4 ligase Buffer | 4 μL |
| Nuclease-free water | QS to 19 μL |
| T4 ligase (2,000 U/μL) | 1 μL |
| Total reaction volume | 20 μL |

5. Mix gently and spin briefly (5 sec.) in microfuge
6. Incubate at room temperature for 2 hours or 16° C. overnight
7. Transform each of the ligation reaction mixtures into XLI Blue Supercompetent cells
8. Pre-chill 14 ml BD Falcon polypropylene round-bottom tubes on ice. Warm SOC medium to 42° C.
9. Thaw the XLI Blue Supercompetent cells on ice. When thawed, gently mix and aliquot 100 ul of cells into each of the pre-chilled tubes.
10. Add 1.7 μL of beta-mercaptoethanol to each aliquot of cells. Incubate the cells on ice of 10 minutes, swirling gently every 2 minutes.
11. Add 2 μL of the ligation reaction mixture to one aliquot of cells. Flick the tubes gently.
12. Incubate the tubes on ice for 30 minutes.
13. Heat-pulse the tubes in a 42° C. water bath for 45 seconds.
14. Incubate the tubes on ice for 2 minutes
15. Add 900 ul of preheated SOC medium and incubate the tubes at 37° C. for 1 hour with shaking at 225-250 rpm.
16. Plate 20 μL and 200 μL of the transformation mixture on LB agar plates containing carbenicillin.
17. Incubate the plates at 37° C. overnight.
Day 3
18. Count colonies and calculate the efficiency and background of the vector as well as the optimal amount of insert for ligation.

Ligate Heavy Chain (HC) Variable Domain into BsaI digested pBA vector Prepare the following ligation reaction in a microcentrifuge tube on ice:

| pBA-BsaI (100 ng) | x μL |
|---|---|
| Heavy chain (HC) variable domain | y μL |
| 5X T4 ligase Buffer | 4 μL |
| Nuclease-free water | QS to 19 μL |
| T4 ligase (2,000 U/μL) | 1 μL |
| Total reaction volume | 20 μL |

1. Mix gently and spin briefly (5 sec.) in microfuge
2. Incubate at room temperature for 2 hours or 16° C. overnight
3. Transform each of the ligation reaction mixtures into XLI Blue Supercompetent cells
4. Pre-chill 14 ml BD Falcon polypropylene round-bottom tubes on ice. Prepare SOC medium to 42° C.
5. Thaw the XLI Blue Supercompetent cells on ice. When thawed, gently mix and aliquot 100 ul of cells into each of the pre-chilled tubes.
6. Add 1.7 μL of beta-mercaptoethanol to each aliquot of cells. Incubate the cells on ice for 10 minutes, swirling gently every 2 minutes.
7. Add 2 μL of the ligation reaction mixture to one aliquot of cells. Flick the tubes gently.
8. Incubate the tubes on ice for 30 minutes.
9. Heat-pulse the tubes in a 42° C. water bath for 45 seconds.
10. Incubate the tubes on ice for 2 minutes
11. Add 900 ul of preheated SOC medium and incubate the tubes at 37° C. for 1 hour with shaking at 225-250 rpm.
12. Plate 20 μL and 200 μL of the transformation mixture on LB agar plates containing carbenicillin.
13. Incubate the plates at 37° C. overnight.
Day 4
14. Count colonies on plates and pick 24 colonies for miniprep and sequencing.
15. Repeat transformations to obtain at least 2000 colonies.
16. Add 6 ml LB medium to each plate containing colonies and gently scrape the bacteria with a spreader to form a dense suspension.
17. Wash each plate with additional 2 ml LB medium to recover residual bacteria.
18. Pool bacteria in a single sterile flask with a cap.
19. Take half of the pooled bacteria and perform plasmid preparation
20. To the remainder of the pooled bacteria, add 0.2 volumes of 80% glycerol and mix thoroughly.
21. Dispense 1-ml aliquots into sterile 1.5 ml microcentrifuge tubes and freeze at −80° C.

Purify pBA-heavy chain variable domain (pBA-HC) library DNA with QIAprep Spin Miniprep kit
1. Resuspend pelleted bacterial cells in 500 μL P1 buffer (with RNase A) and transfer to two microcentrifuge tubes.
2. Add 250 μL P2 buffer and mix thoroughly by inverting the tubes 4-6 times.
3. Add 350 μL N3 buffer and mix immediately and thoroughly by vortexing
4. Centrifuge for 10 min at 13,000 rpm in a microcentrifuge.
5. Apply the supernatants to the QIAprep spin columns by decanting.
6. Centrifuge for 1 min at 13,000 rpm in a microcentrifuge. Discard the flow-through.
7. Wash the QIAprep spin columns by adding 0.75 ml PE buffer.
8. Centrifuge for 1 min at 13,000 rpm in a microcentrifuge.
9. Discard the flow-through and centrifuge for an additional 1 min to remove residue wash buffer.
10. Place the QIAprep columns in a clean 1.5 ml microcentrifuge tubes. To elute DNA, add 50 μL EB buffer to the center of each QIAprep spin column, let stand for 1 min at room temperature.
11. Centrifuge on 2 min at 13,000 rpm in a microcentrifuge.
12. Determine the DNA concentration with spectrophotometer ($OD_{260/280}$).

BsmBI Digestion of pBA-HC Library
Prepare the following digestion reaction in a microcentrifuge tube on ice:

| pBA-HC library DNA (5 μg) | x μL |
|---|---|
| 10X NEB Buffer 3 | 10 μL |
| Nuclease-free water | QS to 97 μL |
| BsmBI (10 U/μl) | 3 μL |
| Total reaction volume | 100 μL |

1. Mix gently and spin briefly (5 sec.) in microfuge
2. Incubate the reaction at 55° C. overnight
Day 5
3. Add 2 µL of Apex phosphatase to the microcentrifuge tube
4. Incubate at 37° C. for 10 minutes
5. Heat at 70° C. for 5 minutes to inactivate the Apex phosphatase Purify BsmBI Digested pBA-HC Library with QIAquick PCR Purification Kit
1. Add 500 µL of Buffer PBI to the microcentrifuge.
2. Mix by vortexing and quick centrifuge.
3. Load 750 µL at a time onto a column.
4. Centrifuge at 12,000×g for 1 minute and decant liquid from collection tube.
5. Repeat until all sample has been processed.
6. Wash with 750 µL PE Buffer (Ethanol added!).
7. Centrifuge at 12,000×g for 1 minute and decant liquid from collection tube.
8. Place column back onto collection tube and centrifuge again.
9. Put column onto new microcentrifuge tubes and elute with 50 µL EB Buffer.

Quality Control Analysis
1. To QC the BsmBI digested pBA-HC library, set up the following reaction in a 1.5 ml micro-centrifuge tube:

| pBA-HC-BsmBI | 2 µl | pBA-HC-uncut | 2 µl |
| --- | --- | --- | --- |
| Water | 7 µl | Water | 7 µl |
| Sample loading buffer | 1 µl | Sample loading buffer | 1 µl |
| Total Volume | 10 µl | Total Volume | 10 µl |

2. Load 10 µl onto a 1% agarose TAE gel with 0.5 µg/ml Ethidium Bromide. Use 1 kb plus DNA ladder as standard. Run the gel at 100V for 20-30 minutes in 1×TAE buffer.
3. Determine the concentration of the BsmBI digested pBA-HC library with spectrophotometer (OD$_{260/230}$).
4. Set up the following control ligation reactions to determine the background and ligation efficiency of the BsmBI digested pBA vector:

| c. Vector Background Ligation | |
| --- | --- |
| pBA-HC-BsmBI (100 ng) | x µL |
| 5X T4 ligase Buffer | 4 µL |
| Nuclease-free water | QS to 19 µL |
| T4 ligase (2,000 U/µL) | 1 µL |
| Total reaction volume | 20 µL |
| d. Test Insert Ligations | |
| pBA-HC-BsmBI (100 ng) | x µL |
| Test insert (5 ng, 10 ng) | y µL |
| 5X T4 ligase Buffer | 4 µL |
| Nuclease-free water | QS to 19 µL |
| T4 ligase (2,000 U/µL) | 1 µL |
| Total reaction volume | 20 µL |

5. Mix gently and spin briefly (5 sec.) in microfuge
6. Incubate at room temperature for 2 hours or 16° C. overnight
7. Transform each of the ligation reaction mixtures into XLI Blue Supercompetent cells
8. Pre-chill 14 ml BD Falcon polypropylene round-bottom tubes on ice. Warm SOC medium to 42° C.
9. Thaw the XLI Blue Supercompetent cells on ice. When thawed, gently mix and aliquot 100 ul of cells into each of the pre-chilled tubes.
10. Add 1.7 ul of beta-mercaptoethanol to each aliquot of cells. Incubate the cells on ice for 10 minutes, swirling gently every 2 minutes.
11. Add 2 ul of the ligation reaction mixture to one aliquot of cells. Flick the tubes gently.
12. Incubate the tubes on ice for 30 minutes.
13. Heat-pulse the tubes in a 42° C. water bath for 45 seconds.
14. Incubate the tubes on ice for 2 minutes
15. Add 900 ul of preheated SOC medium and incubate the tubes at 37° C. for 1 hour with shaking at 225-250 rpm.
16. Plate 20 µL and 200 µL of the transformation mixture on LB agar plates containing carbenicillin.
17. Incubate the plates at 37° C. overnight.
Day 6
18. Count colonies and calculate the efficiency and background of the vector as well as the optimal amount of insert for ligation.

Ligate Light Chain (LC) Variable Domain into BsmBI Digested pBA-HC Library
Prepare the following ligation reaction in a microcentrifuge tube on ice:

| pBA-HC-BsmBI (100 ng) | x µL |
| --- | --- |
| Light chain (LC) variable domain | y µL |
| 5X T4 ligase Buffer | 4 µL |
| Nuclease-free water | QS to 19 µL |
| T4 ligase (2,000 U/µL) | 1 µL |
| Total reaction volume | 20 µL |

1. Mix gently and spin briefly (5 sec.) in microfuge
2. Incubate at room temperature for 2 hours or 16° C. overnight
3. Transform each of the ligation reaction mixtures into XLI Blue Supercompetent cells
4. Pre-chill 14 ml BD Falcon polypropylene round-bottom tubes on ice. Prepare SOC medium to 42° C.
5. Thaw the XLI Blue Supercompetent cells on ice. When thawed, gently mix and aliquot 100 ul of cells into each of the pre-chilled tubes.
6. Add 1.7 ul of beta-mercaptoethanol to each aliquot of cells. Incubate the cells on ice for 10 minutes, swirling gently every 2 minutes.
7. Add 2 ul of the ligation reaction mixture to one aliquot of cells. Flick the tubes gently.
8. Incubate the tubes on ice for 30 minutes.
9. Heat-pulse the tubes in a 42° C. water bath for 45 seconds.
10. Incubate the tubes on ice for 2 minutes
11. Add 900 ul of preheated SOC medium and incubate the tubes at 37° C. for 1 hour with shaking at 225-250 rpm.
12. Plate 20 ul and 200 ul of the transformation mixture on LB agar plates containing Carbenicillin.
13. Incubate the plates at 37° C. overnight.
Day 7
14. Count colonies on plates. Pick 48 colonies for miniprep and sequencing.
15. Repeat transformations to obtain at least 20,000 colonies.
16. Add 6 ml LB medium to each plate containing colonies and gently scrape the bacteria with a spreader for form a dense suspension.
17. Wash each plate with additional 2 ml LB medium to recover residual bacteria.

18. Pool bacteria in a single sterile flask with a cap.
19. To the remainder of the pooled bacteria, add 0.2 volumes of 80% glycerol and mix thoroughly.
20. Dispense 1-ml aliquots into sterile 1.5 ml microcentrifuge tubes and freeze at −80° C.

Example 5. Transfection of Humanization Library into CHO-S Cells

This protocol describes the method of transfecting DNA into CHO-S cells. The estimated time of completion is 3 days with 384 samples per person. Table 4 shows required reagents, consumables and equipment.

TABLE 4

Reagents, Consumables, and Equipment

| Item # | Description | Approved Supplier | Catalogue No. |
|---|---|---|---|
| 1 | Dulbecco's Modified Eagle Medium | Invitrogen | 11965-092 |
| 2 | CD-CHO | Invitrogen | 10743-029 |
| 3 | HT supplement | Invitrogen | 11067-030 |
| 4 | 10 mM MEM Non-Essential Amino Acids | Invitrogen | 11965-092 |
| 5 | Fetal Bovine Serum | Invitrogen | 26140-079 |
| 6 | Lipofeectamine 2000 | Invitrogen | 11668-027 |
| 7 | PBS | Invitrogen | |
| 8 | Opti-MEM Reduced Serum Medium | Invitrogen | 31985-062 |

The following buffers are required for this protocol.
Heat Inactivated Fetal Bovine Serum
500 ml heat inactivated fetal bovine serum in the original vendor bottle
  Heat for 30 minutes at 56° C. with mixing every 5 minutes
  Prepare 50 ml aliquots and store at −20° C.
Serum Supplemented Dulbecco's Modified Eagle Medium
  500 ml Dulbecco's Modified Eagle Medium
  50 ml heat inactivated fetal bovine serum
  5 ml 10 mM MEM Non-Essential Amino Acids
Day 1
1. One week before transfection, transfer CHO-S cells to monolayer culture in serum supplemented Dulbecco's Modified Eagle Medium (D-MEM).
2. One day before transfection, plate $0.4 \times 10^5$ cells in 100 □l of serum supplemented D-MEM per transfection sample in 96 well formats.
Day 2
3. Perform transfection at the end of the work day.
4. For each transfection sample, prepare DNA-Lipofectamine complexes.
5. Dilute 0.2 μg of DNA in 25 μL Opti-MEM Reduced Serum Medium. Mix gently.
6. Dilute 0.5 μL Lipofecctamine in 25 μL Opti-MEM Reduced Serum Medium. Mix gently and incubate for 5 mM at room temperature.
7. Combine the diluted DNA with the diluted Lipofectamine Mix gently and incubate for 20 mM at room temperature.
8. Add the 50 μL DNA-Lipofectamine complexes to each well containing cells and medium. Mix gently by rocking the plate back and forth.
9. Incubate the cells at 37° C. in a 5% $CO_2$ incubator overnight
Day 3
10. Aspirate off medium in each well. Add 100 μL of serum supplemented D-MEM to each well. Collect supernatant for ELISA assay and cell lysate for beta-galactosidase assay.

Example 6. Determination of Expression Levels of Humanized Clones by Quantitation ELISA This protocol describes the method of determining the expression level of antibodies in cell culture supernatant. The estimated time of completion is 2 days with 96 samples per person. Table 5 shows required reagents, consumables and equipment.

TABLE 5

Reagents, Consumables, and Equipment

| Item # | Description | Approved Supplier | Catalogue No. |
|---|---|---|---|
| 1 | Tween-20 | Invitrogen | 11965-092 |
| 2 | Carnation non-fat milk | Local supermarket | |
| 3 | PBS | Irvine Scientific | 9242 |
| 4 | anti-human IgG(H + L)-HRP | Promega | W4031 |
| 5 | Human IgG | Invitrogen | 12000C |
| 6 | Nunc-Immuno Maxisorp 96 well plates | Nalge Nunc | 439454 |
| 7 | Affinity-purified Fc-specific goat anti-human IgG | Sigma | 12136-1 ml |
| 8 | 3,3',5,5'-Tetramethylbenzidine Liquid Substrate | Sigma | T4444 |

The following buffers are required for this protocol.
Washing Solution
0.05% Tween-20 in PBS
Blocking Solution
2% Carnation non-fat milk in PBS
Day 1
11. Coat Nunc-Immuno Maxisorp 96 well plates with 100 μL of 10 μg/ml affinity-purified Fc-specific goat anti-human IgG in coating solution.
12. Cover plates with sealers and incubate overnight at 4° C.
Day 2
13. Decant plates and tap out residue liquid.
14. Add 200 ul washing solution. Shake at 200 rpm for 5 min at room temperature.
15. Decant plates and tap out residue liquid.
16. Add 200 ul blocking solution. Shake at 200 rpm for 1 hour at room temperature.
17. Decant plates and tap out residue liquid.
18. Add duplicates of 100 ul/well of standardized concentration of purified human serum IgG in blocking solution to the plates.
19. Add duplicates of 100 ul of supernatant from the transfection procedure to the plates.
20. Shake at 200 rpm for one hour at room temperature.
21. Decant plates and tap out residual liquid.
22. Add 200 ul washing solution. Shake at 200 rpm for 5 min at room temperature.
23. Repeat step 11-12 3 times.
24. Add 100 ul of 1:5000 dilution of affinity purified goat anti-human antibody conjugate with HRP in blocking solution to each well.

25. Shake at 200 rpm for one hour at room temperature.
26. Decant plates and tap out residual liquid.
27. Add 200 ul washing solution. Shake at 200 rpm for 5 min at room temperature.
28. Repeat step 17-18 3 times.
29. Add 100 ul of Sigma TMB substrate to each well. Incubate at room temperature and check every 2-5 minutes.
30. Add 100 ul 1N HCl to stop the reaction.
31. Read at 450 nm.

Example 7. Determination of Affinity of Humanized Clones by Affinity ELISA

This protocol describes the method of comparing the affinity of antibodies in cell culture supernatant. The estimated time of completion is 2 days with 96 samples per person. Table 6 shows required reagents, consumables and equipment.

TABLE 6

Reagents, Consumables, and Equipment

| Item # | Description | Approved Supplier | Catalogue No. |
|---|---|---|---|
| 1 | Tween-20 | Invitrogen | 11965-092 |
| 2 | Carnation non-fat milk | Local supermarket | |
| 3 | PBS | Irvine Scientific | 9242 |
| 4 | anti-human IgG(H + L)-HRP | Promega | W4031 |
| 5 | Control antibody | Project dependent | |
| 6 | Nunc-Immuno Maxisorp 96 well plates | Nalge Nunc | 439454 |
| 7 | Antigen | Project dependent | |
| 8 | 3,3',5,5'-Tetramethylbenzidine Liquid Substrate | Sigma | T4444 |

The required buffers for this protocol are as described in Example 6.

Day 1
32. Coat Nunc-Immuno Maxisorp 96 well plates with 100 μL of 2 μg/ml antigen in coating solution.
33. Cover plates with sealers and incubate overnight at 4° C.

Day 2
34. Decant plates and tap out residue liquid.
35. Add 200 ul washing solution. Shake at 200 rpm for 5 min at room temperature.
36. Decant plates and tap out residue liquid.
37. Add 200 ul blocking solution. Shake at 200 rpm for 1 hour at room temperature.
38. Decant plates and tap out residue liquid.
39. Add duplicates of 100 ul/well of control antibody (2 μg/ml) in blocking solution to the plates.
40. Add duplicates of 100 ul of supernatant from transfection (SOP 5A) to the plates.
41. Shake at 200 rpm for one hour at room temperature.
42. Decant plates and tap out residual liquid.
43. Add 200 ul washing solution. Shake at 200 rpm for 5 min at room temperature.
44. Repeat step 11-12 3 times.
45. Add 100 ul of 1:5000 dilution of affinity purified goat anti-human antibody conjugate with HRP in blocking solution to each well.
46. Shake at 200 rpm for one hour at room temperature.
47. Decant plates and tap out residual liquid.
48. Add 200 ul washing solution. Shake at 200 rpm for 5 mM at room temperature.
49. Repeat step 17-18 3 times.
50. Add 100 ul of Sigma TMB substrate to each well. Incubate at room temperature and check every 2-5 minutes.
51. Add 100 ul 1N HCl to stop the reaction.
52. Read at 450 nm.

Example 8. Biacore (Surface Plasmon Resonance) Affinity Measurement of BA001 and Humanized Derivatives BIAcore 3000, GE Healthcare, was used to determine binding curves and kinetic parameters. An anti-human Fc (1.8 mg/ml) was diluted to a concentration of 50 ug/ml in NaOAc buffer (10 mM, pH 4.8) and coupled to the carboxymethylated dextran matrix of a CM-5 sensor chip using the manufacturer's amine-coupling chemistry as described in the BIAcore systems manual. Using the surface preparation wizard aiming for 10000RU, the carboxyl groups on the sensor surfaces were first activated with NHS/EDC followed by the addition of the anti-human Fc. The remaining activated groups were blocked by the injection of 1M ethanolamine Each of the flow cells was coupled individually. Employing these conditions, the four flow cell surfaces containing 7554-9571 RU of anti-human Fc were prepared. In preliminary experiments, it was determine that three injections (15 ul at 30 ul/min) 100 mM $H_3PO_4$/0.05% CHAPS would efficiently remove the bound immunoglobulin and preserve the binding capacity of the immobilized anti-human Fc.

Experiments were performed on the BIAcore 3000 at 25° C. and a flow rate of 30 ul/min. The antibody candidate was dissolved in HBS (10 mM HEPES with 0.15M NaCl, 3.4 mM EDTA, and 0.05% surfactant P20 at pH 7.4) at 5 ug/ml. The analyte, IL-6, was dissolved in HBS at 0.25, 0.125, 0.062, 0.031 and 0.015 ug/ml. 3*30 ul of 5 ug/ml of antibody BA001 was flowed over its respective flow cell followed by injections of 240 ul of each IL-6 concentration at 30 ul/min (association phase) and an uninterrupted 1200 seconds of buffer flow (dissociation phase). The surface of the chip was regenerated by three sequential injections of 15 ul each with 100 m M $H_3PO_4$/0.05% CHAPS. The injections of HBS serve as a reference (blank sensogram) for the subtraction of bulk refractive indices for analysis. Using the 1:1 model in BIAeveluation 4.1, both a local fit and global fit was done for both dissociation (kd, [s-1] and association (ka, $[M^{-1}s^{-1}]$) and the dissociation constant (KD, [M]) calculated (kd/ka).

Analysis was done using BIAeveluation version 3.0. Kinetic constants were derived from sensogram data by fitting the experimental curves to the rate equations derived from models of the interaction mechanisms. A global analysis using a 1:1 binding model with local RUmax fit, the ka, kd, and KD were determined.

The following equations were utilized:

$$Ab + Ag \rightleftharpoons AbAg$$

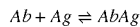

$$K_a = \frac{[AbAg]}{[Ab][Ag]} = \frac{1}{K_d}.$$

Biacore data for humanized anti-IL6 Mabs before affinity maturation is set forth in FIG. 4.

Example 9. Humanized Antibody Preparation from a Template Anti-IL6 Antibody

Sequences for the template antibody and lead hits and fragment nucleic acid and protein sequences are disclosed in US Publication No. 2010/0138945, Humanized Anti-IL-6 Antibodies, Frey et al., which is incorporated herein by reference in its entirety. In this example, the template antibody was BA001; an anti-human IL-6 antibody. Template antibody BA001 is the same sequence, but manufactured in a different expression system, compared to CNTO328, a chimeric, human-murine antibody from US 2006/0257407, which is incorporated herein by reference.

FIG. 1 shows a schematic of the method analogous to that used for humanization of the template antibody BA001. Detailed steps are described in Examples 1-8. The template antibody was cloned, and sequences were identified for each complementarity determining region (CDR). The original CDRs were synthesized; and a synthetic ds DNA fragment library based upon each CDR was prepared. A human framework pool was prepared only from human functionally expressed antibodies obtained from human germline sequences. The CDRs and the human frameworks were assembled, in this case by step wise liquid phase ligation, to form a humanized light chain (LC) variable domain encoding library; and a humanized heavy chain (HC) variable domain encoding library. LC and HC domains were inserted to a vector. In one aspect, the vector contains the sequence which encodes LC and HC framework 4. The vector with the insert is transfected and expressed in a mammalian cell line to prepare a full length human antibody variant library; in this case a human IgG variant library. The library was screened to select humanized antibodies which were comparable or superior to the donor antibody in at least one characteristic, for example antigen affinity or expression level in a mammalian production cell line.

Figure 2:
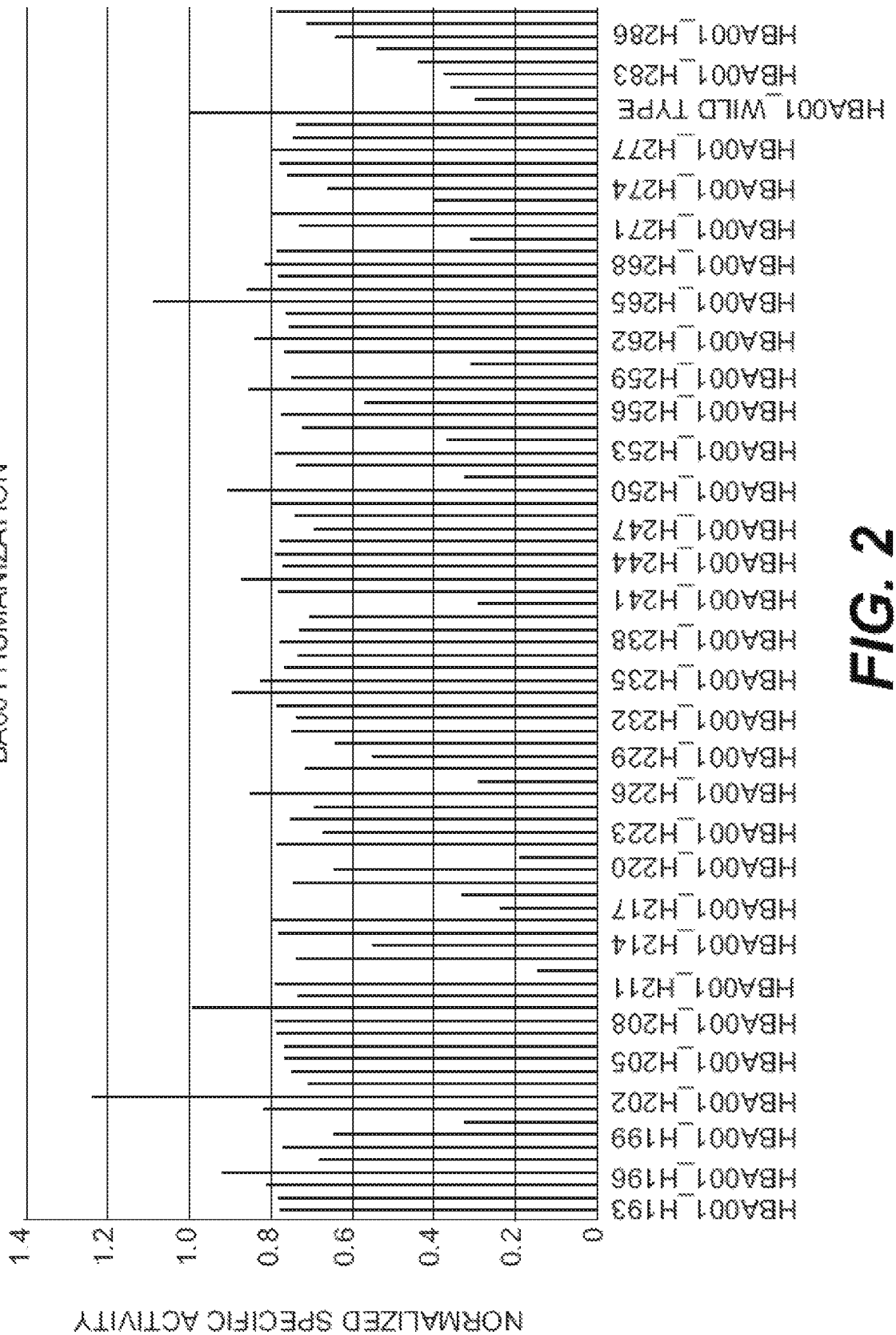
FIG. 2 shows data from the primary screen of humanized variants of template antibody BA001. The primary screen comprised high throughput ELISA of variants compared to the donor antibody, shown with an asterisk. ELISAs were used to determine antigen binding and quantitation.

FIG. 2 shows data from the primary screen of humanized variants of template antibody BA001. The primary screen comprised high throughput ELISA of variants compared to the donor antibody, shown with an asterisk. ELISAs were used to determine antigen binding and quantitation. ELISA protocols are presented in detail in the Examples.

Figure 3:
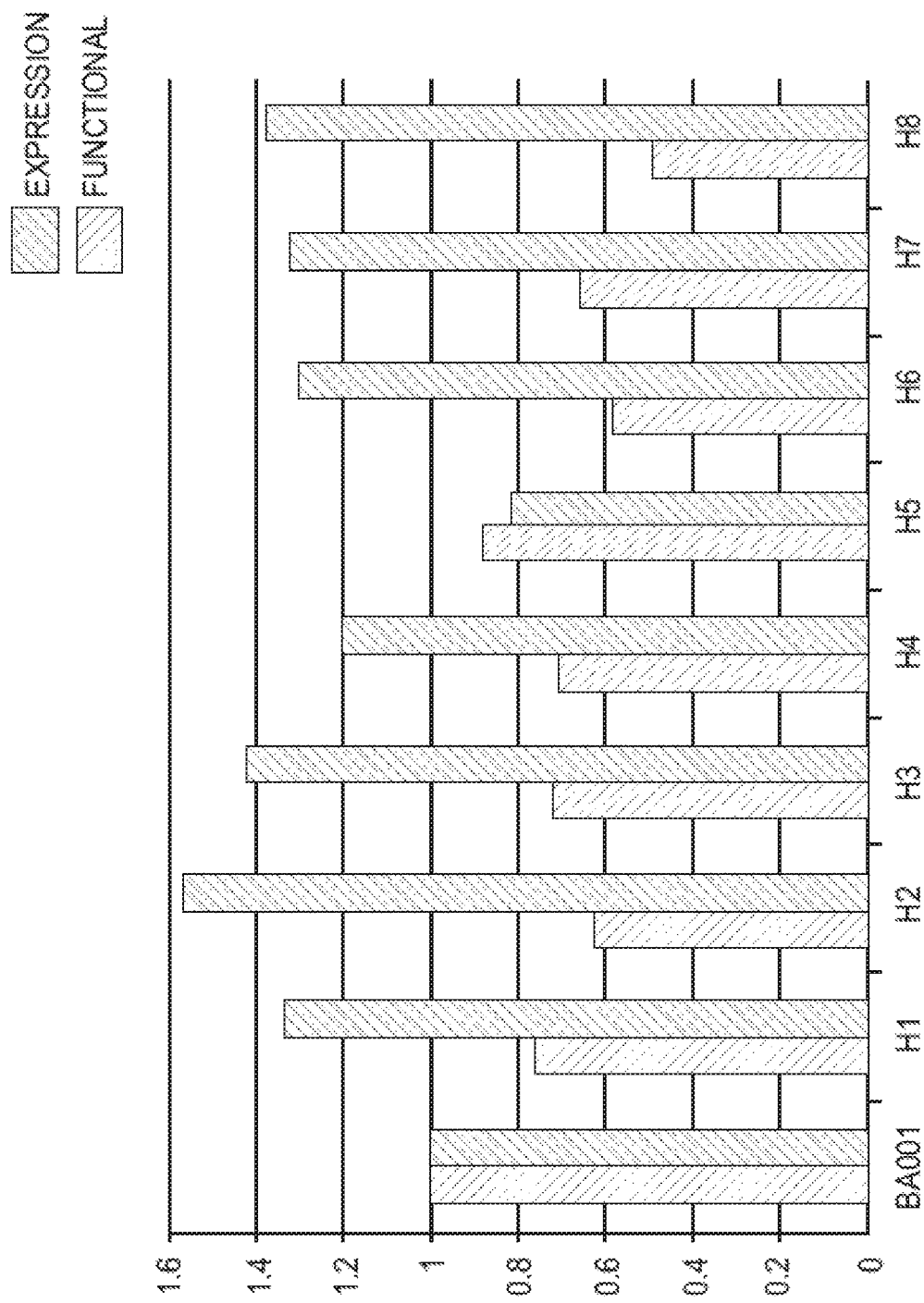
FIG. 3 shows the top 8 confirmed humanized antibody variant hits in terms of both expression and function compared to the template antibody BA001. DNA and protein sequences for BA001 and humanized variants shown are described in U.S. Publication No. US 2010/0138945, which is incorporated herein by reference.

FIG. 3 shows the top 8 confirmed humanized antibody variant hits in terms of both expression and function compared to the template antibody BA001. Selection of hits was based on antigen binding, expression level in a mammalian cell line and sequence diversity. DNA and protein sequences for BA001 and humanized variants shown are described in U.S. Publication No. US 2010/0138945, which is incorporated herein by reference.

FIG. 4 shows binding affinity BiaCore surface plasmon resonance data for humanized anti-IL6 antibodies compared to a template antibody. Data for the template, CNTO328, a chimeric, human-murine antibody, is from US 2006/0257407, which is incorporated herein by reference. BA001 is also a template antibody that has the same sequence as the template CNTO328, but was manufactured in a different expression system. Humanized variant antibodies h1-h8 were obtained with no additional affinity maturation.

Figure 5:
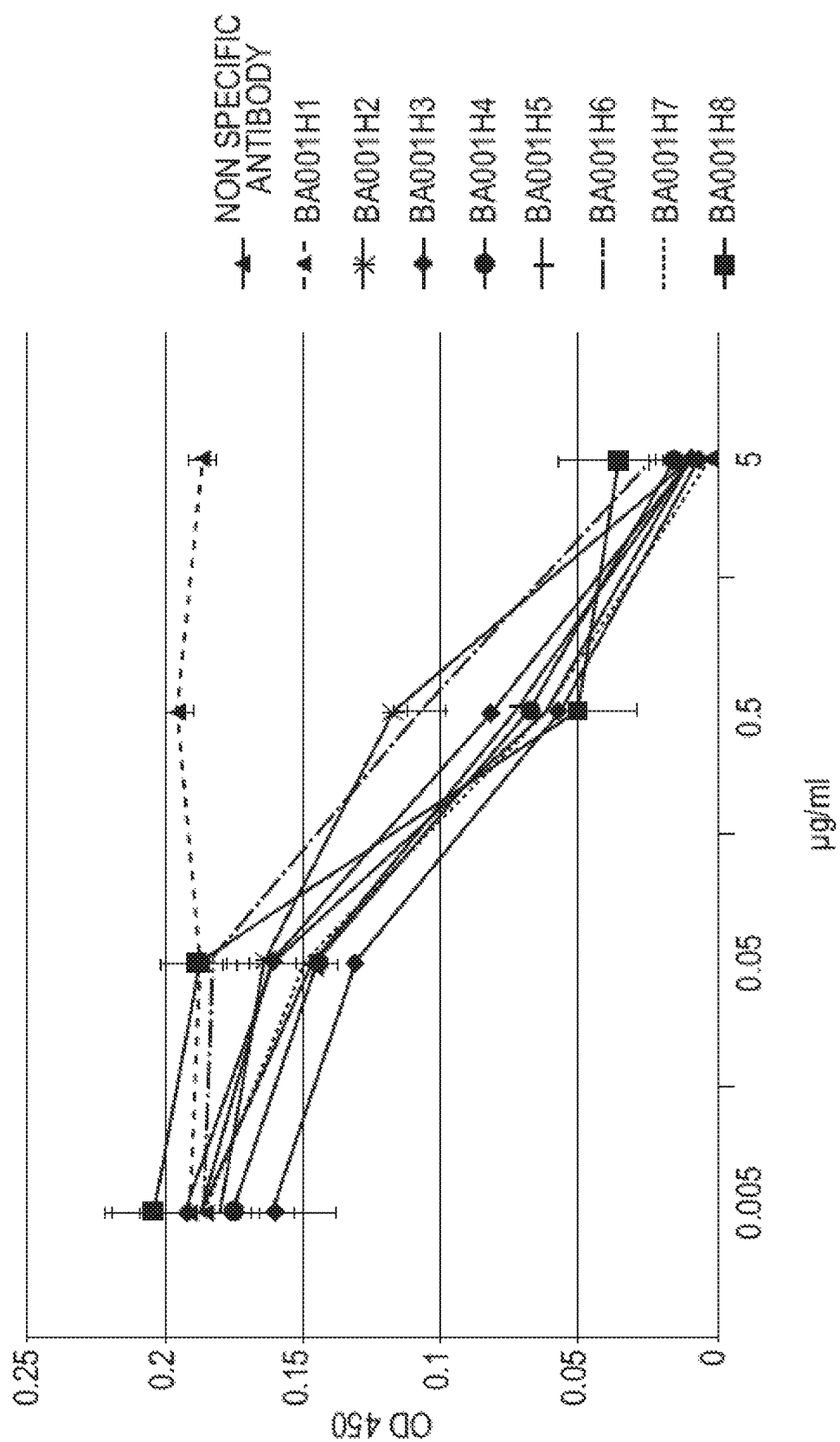
FIG. 5 shows results of an ELISA wherein humanized antibody variants block antigen binding of template antibody BA001.

FIG. 5 shows results of an ELISA wherein humanized antibody variants block antigen binding of template antibody BA001.

It will be clear that the invention can be practiced otherwise than as particularly described in the foregoing description and examples. Numerous modifications and variations of the present invention are possible in light of the above teachings and, therefore, are within the scope of the appended claims.

I claim:

1. A method of producing a humanized antibody from a template antibody, the method comprising:
 (a) synthesizing immunoglobulin heavy chain (HC) double stranded DNA fragment libraries comprising three complementarity determining region (CDR) fragment encoding libraries, an HC CDR1 library, an HC CDR2 library and an HC CDR3 library and three framework (FW) fragment encoding libraries, an HC FW1 library, an HC FW2 library and an HC FW3 library, wherein at least one CDR fragment encoding library comprises a plurality of CDR-encoding DNA fragments derived from the template antibody using an evolution technique independently selected from Comprehensive Positional Evolution, Comprehensive Protein Synthesis, Flex Evolution, Synergy Evolution, Comprehensive Positional Insertion evolution, Comprehensive Positional Deletion evolution, and combinations thereof, and each FW fragment encoding library is selected from a human framework pool obtained from functionally expressed human antibodies;
 (b) synthesizing immunoglobulin light chain (LC) double stranded DNA fragment libraries comprising three CDR fragment encoding libraries, an LC CDR1 library, an LC CDR2 library and an LC CDR3 library and three FW fragment encoding libraries, an LC FW1 library, an LC FW2 library and an LC FW3 library, wherein at least one CDR fragment encoding library comprises a plurality of CDR-encoding DNA fragments derived from the template antibody using an evolution technique independently selected from Comprehensive Positional Evolution, Comprehensive Protein Synthesis, Flex Evolution, Synergy Evolution, Comprehensive Positional Insertion evolution, Comprehensive Positional Deletion evolution, and combinations thereof, and each FW fragment encoding library is selected from a human framework pool obtained from functionally expressed human antibodies;
 (c) assembling from each of the HC double stranded DNA fragment libraries by stepwise liquid phase ligation of heavy chain FW encoding fragments and CDR encoding fragments in the order of: FW1- CDR1- FW2- CDR2- FW3- CDR3 to produce a humanized HC variable domain encoding library comprising one or more polynucleotides;
 (d) assembling from each of the LC double stranded DNA fragment libraries by stepwise liquid phase ligation of light chain FW encoding fragments and CDR encoding fragments in the order of: FW1- CDR1- FW2- CDR2- FW3- CDR3 to produce a humanized LC variable domain encoding library comprising one or more polynucleotides;
 (e) cloning the one or more polynucleotides in the assembled humanized heavy chain variable domain library and the one or more polynucleotides in the assembled light chain variable domain library into an expression vector to create a humanization library;
 (f) transfecting the humanization library into cells; and
 (g) expressing humanized antibodies in the cells to create a humanized antibody library.

2. The method of claim 1 wherein the vector comprises a nucleic acid sequence encoding HC framework region 4.

3. The method of claim 2 wherein the nucleic acid sequence encoding framework 4 is derived from a human heavy chain variable domain derived from a functionally expressed human antibody.

4. The method of claim 1 wherein the vector comprises a nucleic acid sequence encoding LC framework region 4.

5. The method of claim 4 wherein the nucleic acid sequence encoding framework 4 is derived from a human light chain variable domain derived from a functionally expressed human antibody.

6. The method of claim 1 wherein the humanized antibody library has 10,000,000 members or fewer.

7. The method of claim 6 wherein the humanized antibody library has 1,000,000 members or fewer.

8. The method of claim 7 wherein the humanized antibody library has 100,000 members or fewer.

9. The method of claim 1 wherein the cloning step comprises cloning the assembled humanized HC variable domain library into the expression vector to create a vector-HC variable domain DNA library, and ligating the assembled LC variable domain library into the vector-HC library to create the humanization library.

10. The method of claim 1 wherein the expression step comprises expressing both the humanized HC variable domain and the humanized LC variable domain from a single promoter.

11. The method of claim 1 further comprising a step of screening the humanized antibody library in the cells for selection of a humanized antibody having one or more improved characteristics when compared to the template antibody; the one or more improved characteristics being selected from the group consisting of: equilibrium dissociation constant ($K_D$); stability; melting temperature ($T_m$); pI; solubility; expression level; reduced immunogenicity and improved effector function, relative to the template antibody.

12. The method of claim 1 wherein the cells are selected from a eukaryotic cell production host cell line selected from the group consisting of 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells; S. cerevisiae yeast cells; and pichia yeast cells.

13. The method of claim 12 wherein the eukaryotic cell production host cell line is CHO-S or HEK293.

14. The method of claim 12 wherein the eukaryotic cell production host cell line is CHOK1SV or NS0.

15. The method of claim 1 wherein the cells are a eukaryotic cell production host with antibody cell surface display.

16. The method of claim 1 wherein the cells are a eukaryotic cell production host with antibody cell surface display and one or more screening steps is performed in the eukaryotic cell production host.

17. The method of claim 16 wherein the one or more screening steps employ a technique selected from the group consisting of quantitative ELISA, affinity ELISA, ELISPOT, flow cytometry, immunocytology, surface plasmon resonance analysis, kinetic exclusion assay, SDS-PAGE, Western blot, and HPLC.

18. The method of claim 11 further comprising a step of producing the selected humanized antibody in the same cells used in the expressing step.

19. The method of claim 11, wherein the one or more improved characteristics have an improvement that is between about 1% and 500%, relative to a same characteristic of the template antibody or an improvement that is between about 2 fold and 1000 fold, relative to a same characteristic of the template antibody.

20. The method of claim 11, wherein the selected humanized antibody has two or more of said improved characteristic one of which is an enhanced expression level.

* * * * *